United States Patent
Sodeoka et al.

(10) Patent No.: US 6,589,977 B1
(45) Date of Patent: Jul. 8, 2003

(54) PYRROLE DERIVATIVES AND CELL DEATH INHIBITORS

(75) Inventors: Mikiko Sodeoka, Miyagi (JP); Miho Katoh, Kanagawa (JP); Mikako Fujita, Tokushima (JP); Rei Asakai, 430-go, Kitaohmiyajutaku 1-gotoh, 279-1, Dote-cho 1-chome, Ohmiya-shi, Saitama 330-0801 (JP)

(73) Assignees: Sagami Chemical Research Center, Kanagawa (JP); Rei Asakai, Saitama (JP)

(*) Notice: Subject to any disclaimer, the term of this patent is extended or adjusted under 35 U.S.C. 154(b) by 0 days.

(21) Appl. No.: 09/890,827

(22) PCT Filed: Feb. 8, 2000

(86) PCT No.: PCT/JP00/00675

§ 371 (c)(1),
(2), (4) Date: Aug. 6, 2001

(87) PCT Pub. No.: WO00/47575

PCT Pub. Date: Aug. 17, 2000

(30) Foreign Application Priority Data

Feb. 9, 1999 (JP) .......................................... 11-031036

(51) Int. Cl.[7] ..................... A61K 31/404; C07D 403/14
(52) U.S. Cl. ....................................... 514/414; 548/455
(58) Field of Search ........................... 548/455; 514/414

(56) References Cited

FOREIGN PATENT DOCUMENTS

| EP | 0 397 060 | 11/1990 |
| EP | 0 612 742 A1 | 8/1994 |
| WO | WO 99/42100 A1 | 8/1999 |

OTHER PUBLICATIONS

International Search Report.
Chemical Abstracts, vol. 73, abstract No. 130836, Teuber, H.J. et al., "Heterohelicenes from 1,4–cyclohexanedione bis(phenylhyrazone)", Chem. Ber., (1970), 103(10), p. 3319–42.

Hashimoto, T. et al., "Three Novel Dimethyl Pyrroledicarboxylate, Lycogarubins A–C, from the Myxomycetes *Lycogala epidendrum*", Tetrahedron Letters, vol. 35, No. 16, pp. 2559–2560, 1994.

P.D.Davis et al., Journal of Medicinal Chemistry, "Inhibitors of Protein Kinase C. 1.[1] 2,3–Binarylmaleimides" 1992, vol. 35, No. 1, pp. 177–184, XP–000910195.

R.Froede et al., Tetrahedron Letters, "Isolation and Synthesis of 3,4–Bis(indol–3–yl)pyrrole–2,5–dicarboxylic Acid Derivatives from the Sline Mould *Lycogala epidendrum*", 1994, vol. 35, No. 11, pp. 1689–1690, XP–001061526.

T.Hoshino et al., Biosci. Biotech. Biochem. "A New Metabolite of Tryptophan, Chromopyrrolic Acid, Produced by *Chromobacterium violaceum*", 1993, vol. 57(5), pp. 775–781.

*Primary Examiner*—Fiona T. Powers
(74) *Attorney, Agent, or Firm*—Sughrue Mion, PLLC

(57) ABSTRACT

Bisindolylpyrrole derivatives represented by general formula [I] which are useful in inhibiting cell death and expected as being useful as preventives and remedies for the progress of various diseases in the progress and worsening of which cell death participates; and cell death inhibitors, drugs and cell/tissue/organ preservatives containing as the active ingredient these derivatives or pharmaceutically acceptable salts thereof.

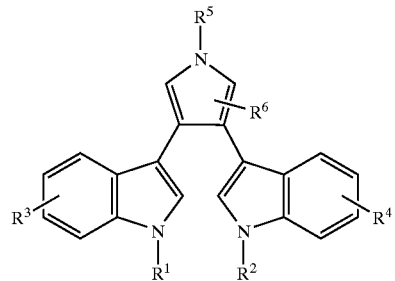

22 Claims, No Drawings

PYRROLE DERIVATIVES AND CELL DEATH INHIBITORS

This application is a 371 of PCT/JP00/00675 filed Feb. 8, 2000.

TECHNICAL FIELD

The present invention relates to a cell death inhibitor capable of inhibiting cell death induced by various substances in living body or foreign stimulants, or stimuli such as temperature, radiation and so on; its use as drugs for treating neurodegenerative diseases, diseases of circulatory organs, hepatitis, renal diseases, inflammatory skin disorders, radiation disorders, viral diseases, prion diseases, functional deficiency of transplanted organs, or the like, or preventing progress of the symptoms of the diseases; use as preservatives for organs, tissues and cells isolated from a living body.

BACKGROUND ART

Recent progress of the study as to cell death have revealed that cell death of cells essential for living body, particularly apoptosis is involved in progress and exacerbation of a variety of diseases (Science, Vol. 267, p. 1456, 1995). Apoptosis is a type of cell death in which cells commit a death using their own molecular machinery, characterized generally by (1) chromatin aggregation, (2) cell shrinkage, (3) blebbing of plasma membrane (formation of processes), (4) nuclear fragmentation, (5) formation of apoptotic bodies, (6) DNA fragmentation, and (7) phagocytosis (scavenging cell debris) by neighboring cells and macrophages. In contrast, there is another type of cell death, called necrosis, characterized by cell swelling and lysis, which occurs without executing the apoptotic processes when cells are exposed to excessive radiation, heat, noxious stimulants or the like. However, the cell death caused by the own molecular machinery does not always show a full set of the apoptosis characteristics described above, depending on species of cells, environments under which cells are present, and species and strength of cell death stimulants. Likewise, necrosis in view of pathology sometimes contains a cell death which some own molecular machinery is responsible for. In the invention, such cell death is also included in apoptosis.

Examples of the diseases whose progress and exacerbation are caused by apoptotic cell death are as follows: neurodegenerative diseases such as Alzheimer's disease [Bio Science terminology library: apoptosis/separate volume of "Jikken Igaku (Experimental Medicine)", p. 168, 1996], spinal muscular atrophy (SMA) [Bio Science terminology library: apoptosis/separate volume of "Jikken Igaku (Experimental Medicine)", p. 173, 1996], amyotrophic lateral screrosis (ALS) [Bio Science terminology library: apoptosis/separate volume of "Jikken Igaku (Experimental Medicine)", p. 176, 1996], Parkinson's disease (J. Neurochem., Vol. 69, p. 1612, 1997), Huntington's disease (J. Neurosci., Vol. 15, p. 3775, 1995), pigmentary degeneration of the retina and glaucoma [Bio Science terminology library: apoptosis/separate volume of "Jikken Igaku (Experimental Medicine)", p. 196, 1996], cerebellar degeneration and neonatal jaundice (Progress in Drug Research, Vol. 48, p. 55, 1997); myasthenia gravis (J. Clinical Investigation, Vol. 99, p. 2745, 1997); brain ischemia from apoplexy and the like, and successive delayed neuronal death (DND) [Bio Science terminology library: apoptosis/separate volume of "Jikken Igaku (Experimental Medicine)", p. 180, p. 182, 1996], ischemic heart disease due to myocardial infarction (myocardial ischemia and disorder after reperfusion), viral myocarditis, autoimmune myocarditis (congestive cardiomyopathy and chronic myocarditis), myocardial disorders or death due to hypertrophic heart and heart failure, arrythmogenic right ventricular cardiomyopathy [Bio Science terminology library: apoptosis/separate volume of "Jikken Igaku (Experimental Medicine)", p. 198, 1996; "Kekkan to Naihi (Blood Vessel and Endothelium), Vol. 7, p. 357, p. 364, p. 370, 1997]; alcoholic hepatitis, viral hepatitis [Bio Science terminology library: apoptosis/separate volume of "Jikken Igaku (Experimental Medicine)", p. 190, 1996], renal diseases such as glomerulonephritis, hemolytic uremic syndrome and the like [Bio Science terminology library: apoptosis/separate volume of "Jikken Igaku (Experimental Medicine)", p. 192, 1996], acquired immunodeficiency syndrome (AIDS) [Bio Science terminology library: apoptosis/separate volume of "Jikken Igaku (Experimental Medicine)", p. 156, 1996; "Ketsueki, Meneki, Shuyou (Blood, Immunity, Cancer)", Vol.2, p. 432, 1997], inflammatory skin disorders such as toxic epidermal necrolysis (TEN) and multiform exudative erythema, alopecia, graft versus host disease (GVH) [Bio Science terminology library: apoptosis/separate volume of "Jikken Igaku (Experimental Medicine)", p. 194, 1996], radiation disorders [Bio Science terminology library: apoptosis/separate volume of "Jikken Igaku (Experimental Medicine)", p. 160, 1996], side effects due to anti-cancer drugs, anti-viral drugs and the like, disorders due to toxic agents such as sodium azide, potassium cyanide and the like [Bio Science terminology library: apoptosis/separate volume of "Jikken Igaku (Experimental Medicine)", p. 162, 1996], sepsis (Critical Care Medicine, Vol. 25, p. 1298, 1997), osteomyelo-dysplasia such as aplastic anemia and the like (Leukemia, Vol. 7, p. 144, 1993), insulin dependent diabetes (Diabetes, Vol. 44, p. 733, 1995), prion diseases such as Creutzfeldt-Jakob's disease (J. Neural Transmission, Supplementum, Vol. 50, p. 191, 1997), and so on. In organ transplantation, it has been suggested that apoptosis due to reactive oxygen species and various chemical mediators generated after reperfusion of anoxic organs by isolation or cardiac arrest of a donor is responsible for functional deficiency of transplanted organs (for example, "Ishoku (Transplantation)", Vol. 27, p. 15, 1992). Probably, rejection reaction after transplantation of an organ, tissues, or cells may be a result of apoptosis of the transplanted cells, which occurs when they are attacked by recipient immune cells. It is thus reasonably concluded that chemical compounds capable of inhibiting cell death can be a promising drug that heals these diseases effectively, or inhibits or stops progress and exacerbation of the symptoms of these diseases.

In the transplantation of organs or tissues, graft survival rate after transplantation depends on the preserving conditions of the organs or tissues isolated from a donor. Accordingly, it is expected to improve organ and tissue preservation by adding chemical compounds inhibiting cell death into preservation liquids for the organs and tissues. Unlike immortalized cells or cancer cells, primary cultured cells isolated from a living body are usually difficult to culture in vitro. For long time cultivation, appropriate concentration of additives including various growth factors are required in the culture medium depending on species of the cells, and apoptosis easily occurs in case that the culture conditions are improper. When cells are cultured for research or medical purposes, it is expected that addition of a chemical compound inhibiting cell death would lead successful cell cultivation.

Apoptosis is known to be triggered by a wide variety of physiological substances such as cytokines including interleukins, hormones including glucocorticoids, excitotoxic amino acids including glutamic acid and NMDA, and membrane proteins represented by Fas ligand, depending on cell types. It is also triggered by deprivation of a specific growth factor or the like in some cell types. There are common apoptosis triggers irrespective of cell type, such as reactive oxygen species generators including hydrogen peroxide and the like, NO generators including SNP and the like, heat, and radiation. A number of chemical compounds are also reported to be able to induce apoptosis. Recent studies have shown that apoptotic signal transduction systems where a variety of signal transduction systems participate at the upstream, appear to converge on caspase activating mechanisms at the downstream, the caspases being a series of cysteine protease (Cell, Vol. 91, p. 443, 1997), though their precise molecular mechanisms should be investigated in future.

Substances heretofore known as apoptosis inhibitors are, depending on species of the cells, a variety of growth factors and nutrient factors, physiological inhibitors such as hormones and the like, antioxidants such as N-acetyl-cysteine and the like, and modified peptide-type caspase inhibitors. Among them, some of peptide-type growth factors and neurotropic factors have been clinically used for the recovery of hematopoietic cells depleted after chemotherapy and for preventing cell death of neurons from neurodegenerative diseases and trauma (Proc. Natl. Acad. Sci. U.S.A., Vol. 90, p. 7951, 1993; Nature, Vol. 367, p. 368, 1994; Proc. Natl. Acad. Sci. U.S.A., Vol. 89, p. 11249, 1992). The antioxidants and caspase inhibitors are only used in experiments of the cell level. Thus, it has been desired to develop an apoptosis inhibitor which is more stable in vivo, orally active, and a non-peptide type as well as low in molecular weight. Furthermore, since it is rare case that all apoptosis-triggering physiological factors and its inhibiting factors of the individual cells have been successfully identified in actual diseases, there is a demand for an entirely new type of cell death inhibitor which is also expected to be beneficial for the diseases where the factors are unidentified.

At present, Euro-Collins' solution and University of Wisconsin solution are generally used as organ preservation solutions for transplantation ("IShoku (Transplantation)", Vol. 27, p. 172, 1992). Supplementation of antioxidants and radical scavengers to such preservation solutions in order to ameliorate damages of reactive oxygen has been reported to have beneficial effects on organ preservation (for example, "IShoku (Transplantation)", Vol. 27, p. 15, 1992; Vol. 26, p. 62, 1991; Vol. 25, p. 596, 1990; Trans Proc., Vol. 17, p. 1454, 1985). However, the organ preservation is not fully sufficient, and higher graft survival rate is still desired.

DISCLOSURE OF THE INVENTION

The invention aims to provide a compound useful for inhibiting death of cells, the drug being expected as a preventive or a remedy for the progress of various diseases wherein cell death participates in progress and exacerbation thereof.

As a result of the extensive studies for achieving the above, the present inventors have found that the below-mentioned bisindolylpyrrole derivatives exhibit a cell death inhibiting action and have accomplished the invention.

Namely, the invention provides a bisindolylpyrrole derivative represented by the following formula [I]

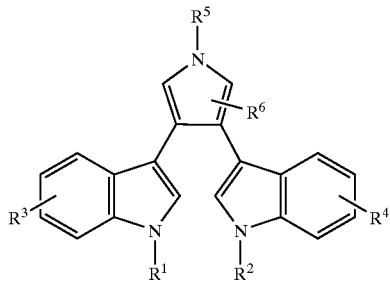

wherein, $R^1$ and $R^2$ each independently represents hydrogen atom, an alkyl group which may possess substituent(s), an alkenyl group which may possess substituent(s), an alkynyl group which may possess substituent(s), an aryl group which may possess substituent(s), an acyl group which may possess substituent(s), an acyloxy group which may possess substituent(s), an alkoxy- or aryloxycarbonyl group which may possess substituent(s), an alkyl- or arylthiocarbonyl group which may possess substituent(s), an aminocarbonyl group which may possess substituent(s), an aminocarbonyloxy group which may possess substituent(s), an alkyl- or arylsulfonyl group which may possess substituent(s), an alkoxyl group which may possess substituent(s), an aryloxy group which may possess substituent(s), or hydroxyl group; $R^3$ and $R^4$ each represents substituent(s) on an indole ring, and represents, number and position (2-, 4-, 5-, 6-, or 7-position as position number of the indole ring) of the substituent(s) and kinds of the substituent(s) may be the same or different, hydrogen atom, an alkyl group which may possess substituent(s), an alkenyl group which may possess substituent(s), an alkynyl group which may possess substituent(s), an aryl group which may possess substituent(s), an acyl group which may possess substituent(s), an acyloxy group which may possess substituent(s), an alkoxy- or aryloxycarbonyl group which may possess substituent(s), an alkoxy- or aryloxycarbonyloxy group which may possess substituent(s), an alkyl- or arylthiocarbonyl group which may possess substituent(s), an aminocarbonyl group which may possess substituent(s), an aminocarbonyloxy group which may possess substituent(s), an alkyl- or arylsulfonyl group which may possess substituent(s), an alkyl- or arylsulfinyl group which may possess substituent(s), an alkoxyl group which may possess substituent(s), an aryloxy group which may possess substituent(s), an alkyl- or arylthio group which may possess substituent(s), hydroxyl group, carboxyl group, oxysulfonyl group, cyano group, nitro group, an amino group which may possess substituent(s), or a halogen atom; $R^1$ and $R^2$, $R^1$ and $R^3$, $R^2$ and $R^4$, $R^3$ and $R^6$, $R^4$ and $R^6$, $R^5$ and $R^6$, two $R^3$, or two $R^4$ may be combined to form a hydrocarbon chain or a hydrocarbon chain containing heteroatom(s) which may possess substituent(s); $R^5$ represents hydrogen atom, an alkyl group which may possess substituent(s), an alkenyl group which may possess substituent(s), an alkynyl group which may possess substituent(s), an aryl group which may possess substituent(s), hydroxyl group, an alkoxyl group which may possess substituent(s), an aryloxy group which may possess substituent(s), an amino group which may possess substituent(s), an acyl group which may possess substituent(s), an acyloxy group which may possess substituent(s), an alkoxy- or aryloxycarbonyl group which may possess substituent(s), an alkyl- or arylthio group which may possess substituent(s), an aminocarbonyl group which may possess substituent(s), an alkyl- or arylsulfonyl group which may possess substituent(s); R⁶ represents substituent(s) on a pyrrole ring (at 2-, 5-, or both position(s) as position numbering of pyrrole ring, in the last case substituents may be the same or different), hydrogen atom, an alkyl group which may possess substituent(s), an alkenyl group which may possess substituent(s), an alkynyl group which may possess substituent(s), an aryl group which may possess substituent(s), an acyl group which may possess substituent(s), an acyloxy group which may possess substituent(s), an aryloxycarbonyl group which may possess substituent(s), an aryloxycarbonyloxy group which may possess substituent(s), an alkyl- or arylthiocarbonyl group which may possess substituent(s), an aminocarbonyl group which may possess substituent(s), an aminocarbonyloxy group which may possess substituent(s), an alkyl- or arylsulfonyl group, an alkyl- or arylsulfinyl group which may possess substituent(s), an alkoxyl group which may possess substituent(s), an aryloxy group which may possess substituent(s), an alkyl- or arylthio group which may possess substituent(s), hydroxyl group, carboxyl group, oxysulfonyl group, cyano group, nitro group, an amino group which may possess substituent(s), or a halogen atom.

The invention also provides a cell death inhibitor comprising, as an active ingredient, a bisindolylpyrrole derivative represented by the following formula [II] or a pharmaceutically acceptable salt thereof

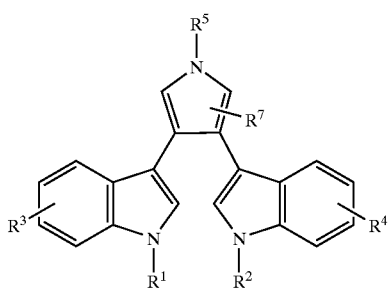

[II]

wherein, R¹ and R² each independently represents hydrogen atom, an alkyl group which may possess substituent(s), an alkenyl group which may possess substituent(s), an alkynyl group, which may possess substituent(s), an aryl group which may possess substituent(s), an acyl group which may possess substituent(s), an acyloxy group which may possess substituent(s), an alkoxy- or aryloxycarbonyl group which may possess substituent(s), an alkyl- or arylthiocarbonyl group which may possess substituent(s), an aminocarbonyl group which may possess substituent(s), an aminocarbonyloxy group which may possess substituent(s), an alkyl- or arylsulfonyl group which may possess substituent(s), an alkoxyl group which may possess substituent(s), an aryloxy group which may possess substituent(s), or hydroxyl group; R³ and R⁴ each represents substituent(s) on an indole ring, and represents, number and position (2-, 4-, 5-, 6-, or 7-position as position number of the indole ring) of the substituent(s) and kinds of the substituent(s) may be the same or different, hydrogen atom, an alkyl group which may possess substituent(s), an alkenyl group which may possess substituent(s), an alkynyl group which may possess substituent(s), an aryl group which may possess substituent(s), an acyl group which may possess substituent(s), an acyloxy group which may possess substituent(s), an alkoxy- or aryloxycarbonyl group which may possess substituent(s), an alkoxy- or aryloxycarbony-loxy group which may possess substituent(s), an alkyl- or arylthiocarbonyl group which may possess substituent(s), an aminocarbonyl group which may possess substituent(s), an aminocarbonyloxy group which may possess substituent(s), an alkyl- or arylsulfonyl group which may possess substituent(s), an alkyl- or arylsulfinyl group which may possess substituent(s), an alkoxyl group which may possess substituent(s), an aryloxy group which may possess substituent(s), an alkyl- or arylthio group which may possess substituent(s), hydroxyl group, carboxyl group, oxysulfonyl group, cyano group, nitro group, an amino group which may possess substituent(s), or a halogen atom; R¹ and R², R¹ and R³, R² and R⁴, R³ and R⁷, R⁴ and R⁷, R⁵ and R⁷, two R³, or two R⁴ may be combined to form a hydrocarbon chain or a hydrocarbon chain containing heteroatom(s) which may possess substituent(s); R⁵ represents hydrogen atom, an alkyl group which may possess substituent(s), an alkenyl group which may possess substituent(s), an alkynyl group which may possess substituent(s), an aryl group which may possess substituent(s), hydroxyl group, an alkoxyl group which may possess substituent(s), an aryloxy group which may possess substituent(s), an amino group which may possess substituent(s), an acyl group which may possess substituent(s), an acyloxy group which may possess substituent(s), an alkoxy- or aryloxycarbonyl group which may possess substituent(s), an alkyl- or arylthiocarbonyl group which may possess substituent(s), an aminocarbonyl group which may possess substituent(s), an alkyl- or arylsulfonyl group which may possess substituent(s); R⁷ represents substituent(s) on a pyrrole ring (at 2-, 5-, or both position(s) as position nymbering of pyrrole ring, in the last case substituents may be the same or different), hydrogen atom, an alkyl group which may possess substituent(s), an alkenyl group which may possess substituent(s), an alkynyl group which may possess substituent(s), an aryl group which may possess substituent(s), an acyl group which may possess substituent(s), an acyloxy group which may possess substituent(s), an alkoxy- or an aryloxycarbonyl group which may possess substituent(s), an alkoxy- or an aryloxy-carbonyloxy group which may possess substituent(s), an alkyl- or arylthiocarbonyl group which may possess substituent(s), an aminocarbonyl group which may possess substituent(s), an aminocarbonyloxy group which may possess substituent(s), an alkyl- or arylsulfonyl group, an alkyl- or arylsulfinyl group which may possess substituent(s), an alkoxyl group which may possess substituent(s), an aryloxy group which may possess substituent( s), an alkyl- or arylthio group which may possess substituent(s), hydroxyl group, carboxyl group, oxysulfonyl group, cyano group, nitro group, an amino group which may possess substituent(s), or a halogen atom; a drug for treating or preventing progress of symptoms, through inhibiting death of neurons, of neurodegenerative diseases such as Alzheimer's disease, spinal muscular atrophy (SMA), amyotrophic lateral screrosis (ALS), Parkinson's disease, Huntington's disease, pigmentary degeneration of the retina, glaucoma, or cerebellar degeneration; a drug for treating or preventing progress of symptoms, through inhibiting death of neurons, of neonatal jaundice; a drug for treating or preventing progress of symptoms, through inhibiting death of cells, of myasthenia gravis; a drug for treating or preventing progress of symptoms, through inhibiting death of neurons, of brain ischemia from apoplexy and the like, and successive delayed neuronal death (DND); a drug for treating or preventing progress of symptoms, through inhibiting death of myocardial cells, of ischemic heart disease due to myocardial infarction, viral myocarditis, autoimmune myocarditis, myocardial disorders or death due to hypertrophic heart and heart failure, or arrythmogenic right ventricular cardiomyopathy; a drug for treating or preventing progress of symptoms, through inhibiting death of hepatic cells, of alcoholic hepatitis or viral hepatitis; a drug for treating or preventing progress of symptoms, through inhibiting death of renal cells, of renal diseases such as glomerulonephritis, hemolytic uremic syndrome and the like; a drug for treating or preventing progress of symptoms, through inhibiting excessive death of T-cells, of acquired immunodeficiency syndrome (AIDS); a drug for treating or preventing progress of symptoms, through inhibiting cell death, of inflammatory skin disorders such as toxic epidermal necrolysis (TEN), multiform exudative erythema and the like, alopecia, or graft versus host disease (GVH); a drug for treating or preventing disorders or side effects, through inhibiting cell death, of radiation disorders or disorders due to toxic agents including side effects due to drugs such as anti-cancer drugs, anti-viral drugs and the like; a drug for treating or preventing progress of symptoms, through inhibiting cell death, of sepsis; a drug for treating or preventing progress of symptoms, through inhibiting death of cells derived from bone marrow, of osteomyelo-dysplasia such as aplastic anemia and the like; a drug for treating or preventing progress of symptoms, through inhibiting cell death, of insulin dependent diabetes; a drug for treating or preventing progress of symptoms, through inhibiting death of neurons, of prion diseases; a drug for treating or preventing functional deficiency of transplanted organs, tissues or cells at transplantation of organs, tissues or cells; a preservative for organs, tissues and cells.

The following will explain the invention in detail.

BEST MODE FOR CARRYING OUT THE INVENTION

The bisindolylpyrrole derivatives according to the invention can be synthesized according to the methods shown in Examples.

In the present description, the alkyl group in the "an alkyl group which may possess substituent(s)" may be any of linear, branched, or cyclic one, and may be exemplified by an alkyl group having 1 to 30 carbon atoms, more concretely, methyl group, ethyl group, propyl group, isopropyl group, butyl group, isobutyl group, s-butyl group, t-butyl group, pentyl group, isopentyl group, neopentyl group, hexyl group, heptyl group, octyl group, nonyl group, decyl group, cyclopropyl group, cyclobutyl group, cyclopentyl group, cyclohexyl group, cycloheptyl group, undecyl group, dodecyl group, tridecyl group, tetradecyl group, pentadecyl group, hexadecyl group, 14-methylpentadecyl group, 6-methylpentadecyl group, octadecyl group, eicosyl group, tetracosyl group, and the like.

In the present description, the alkenyl group in the "an alkenyl group which may possess substituent(s)" may be any of linear, branched, or cyclic one, and may be exemplified by an alkenyl group having 2 to 30 carbon atoms. Concrete examples thereof include allyl group, vinyl group, crotyl group, 1-penten-1-yl group, 2-penten-1-yl group, 3-penten-1-yl group, 1-hexen-1-yl group, 2-hexen-1-yl group, 3-hexen-1-yl group, 2-cyclohexenyl group, 2-cyclopentenyl group, 8-heptadecen-1-yl group, 8,11-heptadecadien-1-yl group, 8,11,14-heptadecatrien-1-yl group, 4,7,10,13-nonadecatetraen-1-yl group, 9-octadecen-1-yl group, 9,12-octadecadien-1-yl group, 9,12,15-octadecatrien-1-yl group, 6,9,12-octadecatrien-1-yl group, 5,8,11,14-eicosatetraen-1-yl group, 5,8,11,14,17-eicosapentaen-1-yl group, and 4,7,10,13,16,19-docosahexane-1-yl group.

In the present description, the alkynyl group in the "an alkynyl group which may possess substituent(s)" may be any of linear, branched, or cyclic one, and may be exemplified by an alkynyl group having 2 to 30 carbon atoms. Concrete examples thereof include ethynyl group, propargyl group, 1-pentyn-1-yl group, 2-pentyn-1-yl group, 3-pentyn-1-yl group, 1-octyn-1-yl group, and 8-heptadecyn-1-yl group.

In the present description, the aryl group in the "an aryl group which may possess substituent(s)" includes a heteroaryl group, and may be exemplified by phenyl group, naphthyl group, anthranyl group, pyrenyl group, biphenyl group, 4-pyridyl group, 2-pyridyl group, pyrimidinyl group, pyrazinyl group, piperazinyl group, pyrazolyl group, imidazolyl group, quinolyl group, pyrrolyl group, indolyl group, furyl group and the like.

In the present description, the acyl group in the "an acyl group which may possess substituent(s)" or "an acyloxy group which may possess substituent(s)" may be any of linear, branched, cyclic, saturated, unsaturated, aliphatic or aromatic one, and may be exemplified by an acyl group having 2 to 30 carbon atoms, more concretely, acetyl group, propionyl group, isopropionyl group, pivaloyl group, oleoyl group, cyclohexylcarbonyl group, acryloyl group, crotonoyl group, benzoyl group, naphthoyl group, nicotinoyl group, and the like.

In the present description, the alkoxy- or aryloxycarbonyl group in the "an alkoxy- or aryloxycarbonyl which may possess substituent(s)" or "an alkoxy- or aryloxycarbonyloxy which may possess substituent(s)" may be any of linear, branched, cyclic, saturated, unsaturated, aliphatic or aromatic one. The examples include methoxycarbonyl group, ethoxycarbonyl group, propyloxycarbonyl group, isopropyloxycarbonyl group, butoxycarbonyl group, s-butoxycarbonyl group, t-butoxycarbonyl group, cyclopentyloxycarbonyl group, cyclohexyloxycarbonyl group, benzyloxycarbonyl group, allyloxycarbonyl group, phenyloxycarbonyl group, pyridyloxycarbonyl group, and the like.

In the present description, the alkyl- or arylthiocarbonyl group in the "an alkyl- or arylthiocarbonyl which may possess substituent(s)" may be any of linear, branched, cyclic, saturated, unsaturated, aliphatic or aromatic one. The examples include methylthiocarbonyl group, ethylthiocarbonyl group, propylthiocarbonyl group, isopropylthiocarbonyl group, butylthiocarbonyl group, t-butylthiocarbonyl group, cyclopentylthiocarbonyl group, cyclohexylthiocarbonyl group, benzylthiocarbonyl group, phenylthiocarbonyl group, pyridylthiocarbonyl group, and the like.

In the present description, the aminocarbonyl group in the "an aminocarbonyl which may possess substituent(s)" or "an aminocarbonyloxy which may possess substituent(s)" may be an unsubstituted carbamoyl group, or an carbamoyl which is substituted by alkyl group(s) which may possess substituent(s), aromatic group(s) which may possess substituent(s), hydroxyl group, alkoxyl group(s) which may possess substituent(s), amino group(s) which may possess substituent(s), and the like. The examples include carbamoyl group, ethylaminocarbonyl group, propylaminocarbonyl group, isopropylaminocarbonyl group, butylaminocarbonyl group, t-butylaminocarbonyl group, cyclopentylaminocarbonyl group, cyclohexylaminocarbonyl group, benzylaminocarbonyl group, phenylaminocarbonyl group, pyridylaminocarbonyl group, and the like.

In the present description, the alkyl- or arylsulfonyl group in the "an alkyl or arylsulfonyl which may possess substituent(s)" may be any of linear, branched, cyclic, saturated, unsaturated, aliphatic or aromatic one. The examples include methanesulfonyl group, ethanesulfonyl group, benzenesulfonyl group, cyclohexanesulfonyl group, naphthalenesulfonyl group, and the like.

In the present description, the alkyl- or arylsulfinyl group in the "an alkyl- or an arylsulfinyl which may possess substituent(s)" may be any of linear, branched, cyclic, saturated, unsaturated, aliphatic or aromatic one. The examples include methanesulfinyl group, ethanesulfinyl group, benzenesulfinyl group, cyclohexanesulfinyl group, naphthalenesulfinyl group, and the like.

In the present description, the alkoxyl group or aryloxy group in the "an alkoxyl group or an aryloxy group which may possess substituent(s)" may be any of linear, branched, cyclic, saturated, unsaturated, aliphatic or aromatic one, and may be exemplified by an alkoxy group or an aryloxy group having 2 to 30 carbon atoms. The particular examples include methoxy group, ethoxy group, propyloxy group, t-butoxy group, allyloxy group, cyclopentyloxy group, cyclohexyloxy group, benzyloxy group, phenoxy group, and the like.

In the present description, the alkyl- or arylthio group in the "an alkyl- or arylthio which may possess substituent(s)" may be any of linear, branched, cyclic, saturated, unsaturated, aliphatic or aromatic one, and may be exemplified by an alkyl- or arylthio group having 2 to 30 carbon atoms. The particular examples include methylthio group, ethylthio group, propylthio group, t-butylthio group, allylthio group, cyclopentylthio group, cyclohexylthio group, benzylthio group, phenylthio group, and the like.

In the present description, the "an amino group which may possess substituent(s)" may be an unsubstituted amino group, or an amino group which is substituted by alkyl group(s), aromatic group(s), and the like. The examples include ethylamino group, propylamino group, isopropylamino group, butylamino group, t-butylamino group, benzylamino group, phenylamino group, pyridylamino group, piperazinyl group, indolinyl group, and the like.

In the present description, "a halogen atom" may be fluorine atom, chlorine atom, bromine atom, and iodine atom.

The examples of substituents which may be present in the above-mentioned alkyl group, alkenyl group, alkynyl group, aryl group, acyl group, acyloxy group, alkoxy- or aryloxycarbonyl group, alkoxy- or aryloxycarbonyloxy group, alkylthio- or arylthiocarboyl group, aminocarbonyl group, aminocarbonyloxy group, alkoxyl group or aryloxy group, alkyl- or arylthio group, alkyl or arylsulfonyl group, alkyl or arylsulfinyl group, amino group, and the like include alkyl groups, alkenyl groups, alkynyl groups, aryl groups, acyl groups, acyloxy group, alkoxy- or aryloxycarbonyl group, alkoxy or aryloxycarbonyloxy group, alkylthio- or arylthiocarbonyl group, aminocarbonyl group, aminocarbonyloxy group, alkoxyl group, aryloxy group, alkyl- or arylthio group, alkyl- or arylsulfonyl group, alkyl- or arylsulfinyl group, and particular examples thereof are the same as mentioned above. The other substituents may be exemplified by halogen groups, nitro group, amino groups (which may possess substituent(s) such as acyl group(s), alkoxy- or aryloxycarbonyl group(s), carbamoyl group(s), substituted sulfonyl group(s), alkyl group(s), cycloalkyl group(s), aryl group(s), and the like), cyano group, hydroxyl group, carboxyl group, oxysulfonyl group, epoxy group and the like, as well as aralkyl groups such as benzyl group, phenethyl group, naphthylmethyl group, and the like.

As examples of two $R^3$ groups or two $R^4$ groups combined to form a hydrocarbon chain or a hydrocarbon chain containing heteroatom(s) which may possess substituent(s), rings fused to the benzene ring of the indole are represented. The fused ring may be exemplified by saturated or unsaturated aliphatic ring such as cyclopentane ring, cyclohexane ring, cyclohexene ring and the like; saturated or unsaturated heterocyclic ring such as pyrrolidine ring, tetrahydrofuran ring, imidazolidine ring, imidazoline ring, piperidine ring, morpholine ring, tetrahydrothiophene ring, and the like; aromatic ring such as benzene ring, naphthalene ring, indane ring, acenaphthene ring, fluorene ring, phenanthrene ring, and the like; heteroaromatic ring such as furan ring, thiophene ring, pyrrole ring, imidazole ring, pyridine ring, pyrimidine ring, pyradine ring, benzofuran ring, indole ring, quinoline ring, and the like.

As to the pharmaceutically acceptable salts, the compound having an acid part may formed a salt with an inorganic base or organic base, for example, an alkaline metal salt such as sodium salt, potassium salt, or the like; an alkaline earth metal salt such as calcium salt, magnesium salt, or the like; ammonium salt; an aliphatic or heteroaromatic amine salt such as triethylamine salt, ethanolamine salt, lysine salt, arginine salt, quinoline salt, pyridine salt or the like; a quaternary ammonium salt such as tetramethylammonium or the like. The compound having a basic part may form a salt with an inorganic or organic acid, for example, hydrochloride, bromate, iodate, sulfate, nitrate, phosphate, citrate, tartrate, malate, lactate, salicylate, malonate, fumarate, succiniate, oxalate, ascorbate, or the like.

The compound according to the invention may be applied as medicament in any form selected from various forms, for example, formulations for oral administration such as tablets, capsules, powders, granules, or liquids; and formulations for parenteral administration such as injections, rectal suppositories, formulations for external use on skin, inhalant, and the like.

Solid formulations can be prepared in a form of tablets, capsules, granules, or powders by themselves, or can be prepared with using suitable additive(s). Examples of such additives include sugars such as lactose or glucose; starches; fatty acids such as stearic acid; inorganic salts such as magnesium metasilicate aluminate or anhydrous calcium phosphate; synthetic polymers such as polyvinylpyrrolidone or polyalkylene glycol; fatty acid salts such as calcium stearate or magnesium stearate; alcohols such as stearyl alcohol or benzyl alcohol; synthetic cellulose derivatives such as methyl cellulose, ethyl cellulose, carboxymethyl cellulose, or hydroxypropyl cellulose; other conventional additives such as water, gelatin, talc, vegetable oils, acacia, or the like.

Liquid formulations are prepared in a form of suspensions, syrups, or injections by using suitable additive (s) conventionally used in liquid formulations such as water, alcohols, vegetable-derived oils including soybean oil, peanut oil, sesame oil, etc.

Especially, examples of suitable solvents for injections include distilled water for injection, aqueous lidocain hydrochloride solution, physiological saline, aqueous glucose solution, ethanol, liquids for intravenous injection such as aqueous solutions of citric acid and sodium citrate, electrolyte solution, and the like, or mixtures thereof. These injections may be a form of pre-dissolved one, and also a form for dissolving before use, which is composed of powder itself or powder with suitable additive(s).

The rectal suppositories may be prepared either by melting an active ingredient and base material(s) such as cacao butter, tri-, di- and monoglyceride of a fatty acid, polyethylene glycol, and the like under heating; charging the melt into a mold; and then cooling it; or by dissolving an active ingredient into polyethylene glycol, soybean oil, or the like and then covering it with gelatin film.

In the preparation of formulations for external use on skin, an active ingredient is added to vaseline, bees wax, liquid paraffin, polyethylene glycol, etc., followed by either kneading it, if necessary under heating, to form ointments, or kneading it with an adhesive such as rosin, a polymer of alkyl acrylate, etc. and spreading the kneaded one on unwoven cloth such as polyethylene or the like to form tapes.

In the preparation of inhalant, an active ingredient is dissolved or dispersed into a propellant such as flon gas, and then a pressure container is filled up to form aerosols.

Preferred dosage of the compound according to the invention varies depending on kinds of the compositions blended, dosing times and diseases to be treated, and also ages, body weights, and symptoms of patients, but may be ordinarily in an amount of about 1–1000 mg a day, preferably 5 to 500 mg, and they may be administered in one or several dosage units per day.

The organs relating to the invention may be all organs, such as heart, lung, liver, kidney, pancreas, and intestine.

The tissues relating to the invention may be all tissues, such as skin, cornea, bone marrow, vascular systems, and bone.

In the invention, cells expected to have effects on maintenance of the cell function by transplantation or the preservation may be all types of cells (normal various cells, immortalized cell lines, cancer cells, and cells that are modified by genetic recombination techniques for disease treatment and research purposes), such as vascular cells, islet cells of Langerhans, epidermal cells, neuronal cell, and embryonic stem cells.

As far as an administration method is concerned, when the chemical compounds according to the invention are used for the preservation of organs, tissues, and cells, various routes can be selected. For example, the present compound or a pharmaceutically acceptable salt thereof can be added to a culture medium or preservation solution containing appropriate salts and nutrients. In case of organ transplantation, it can be also administered intravenously or at perfusion to a donor prior to the organ isolation.

The invention will be explained in detail in the following sections by way of Examples but the invention is, needless to say, not limited to the Examples.

EXAMPLES

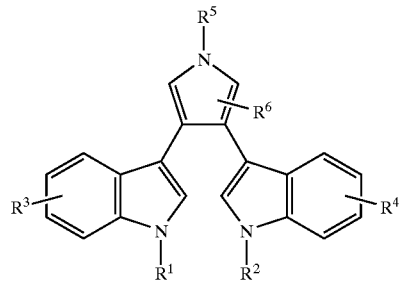

| Compound No. | $R^1$ | $R^2$ | $R^3$ | $R^4$ | $R^5$ | $R^6$ |
|---|---|---|---|---|---|---|
| 1 | H | H | H | H | $CH_3$ | H |
| 2 | COO$^t$Bu | H | H | H | $CH_3$ | H |
| 3 | COO$^t$Bu | COO$^t$Bu | H | H | $CH_3$ | H |
| 4 | $(CH_2)_3NH_2$ | H | H | H | $CH_3$ | H |
| 5 | $(CH_2)_3NH_2$ | $(CH_2)_3NH_2$ | H | H | $CH_3$ | H |
| 6 | $(CH_2)_3N(CH_3)_2$ | H | H | H | $CH_3$ | H |
| 7 | $(CH_2)_3N(CH_3)_2$ | $(CH_2)_3N(CH_3)_2$ | H | H | $CH_3$ | H |
| 8 | $CH_3$ | H | H | H | $CH_3$ | H |
| 9 | $CH_3$ | $CH_3$ | H | H | $CH_3$ | H |
| 10 | H | H | 7-$CH_3$ | 7-$CH_3$ | $CH_3$ | H |
| 11 | H | H | 2-$CH_3$ | 2-$CH_3$ | $CH_3$ | H |
| 12 | H | H | 5-F | 5-F | $CH_3$ | H |
| 13 | H | H | 5-$OCH_3$ | 5-$OCH_3$ | $CH_3$ | H |
| 14 | $CH_3$ | $CH_3$ | 5-$OCH_3$ | 5-$OCH_3$ | $CH_3$ | H |
| 15 | H | H | 5-$CH_3$ | 5-$CH_3$ | $CH_3$ | H |
| 16 | $(CH_2)_3NH_2$ | $CH_3$ | 5-$CH_3$ | 5-$CH_3$ | $CH_3$ | H |
| 17 | H | H | H | H | $C_6H_5$ | H |
| 18 | H | H | H | H | $CH_2C_6H_5$ | H |
| 22 | H | COO$^t$Bu | 5-$CH_3$ | 5-$CH_3$ | $CH_3$ | H |
| 23 | COO$^t$Bu | COO$^t$Bu | 5-$CH_3$ | 5-$CH_3$ | $CH_3$ | H |
| 24 | H | $CH_3$ | 5-$CH_3$ | 5-$CH_3$ | $CH_3$ | H |

-continued
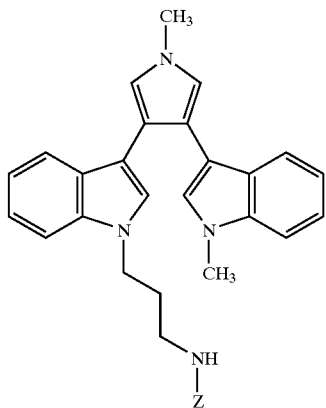
Z = 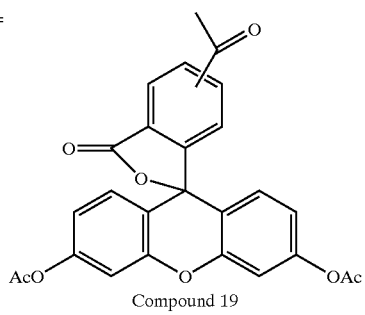
Compound 19
Z = 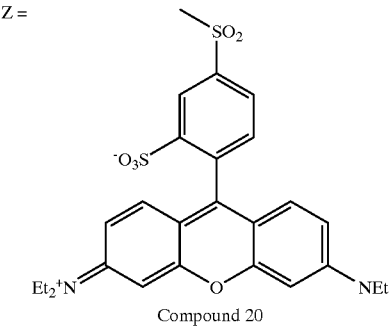
Compound 20
Z = 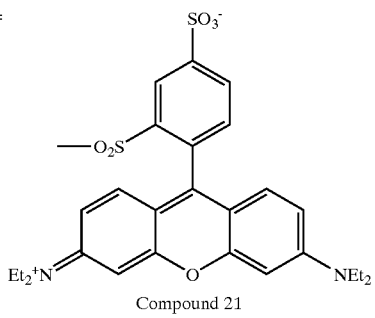
Compound 21

Example 1

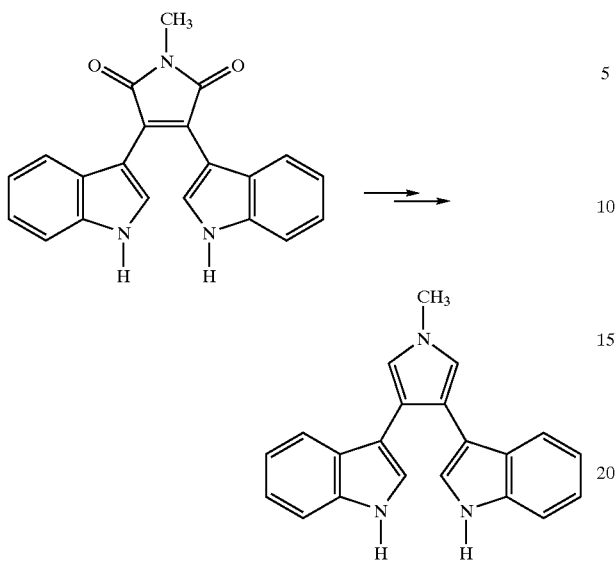

To a solution of 2,3-bis(1H-indol-3-yl)-N-methylmaleimide (14 mg, 0.04 mmol) synthesized according to a known method (Tetrahedron, Vol. 44, p. 2887, 1988) in DMF (1 mL) was added a small amount of 10% palladium-carbon and the whole was stirred at room temperature for 1 day under hydrogen atmosphere. The palladium-carbon was removed by filtration, and the filtrate was concentrated under reduced pressure. The residue was purified by column chromatography over silica gel (ethyl acetate:n-hexane=2:1) to obtain 3,4-bis(1H-indol-3-yl)-1-methy-2,5-dioxopyrrolidine (12.9 mg, 91.7%) as a mixture of two isomers (A:B=2.7:1.0) as pale red solids.

A] $^1$H-NMR(CDCl$_3$): δ 3.28(s, 3H), 4.77(s, 2H), 6.60–7.40(m, 10H), 7.68(brs, 2H). B] $^1$H-NMR(CDCl$_3$): δ 3.26(s, 3H), 4.41(s, 2H), 6.60–7.40(m, 10H), 8.15(brs, 2H). MS m/z 343(M$^+$).

To a solution of 3,4-bis(1H-indol-3-yl)-1-methyl-2,5-dioxopyrrolidine (300 mg, 0.09 mmol) in THF (0.5 mL) was added 0.95M diisobutylaluminum hydride (0.36 mL, 0.35 mmol) dropwise slowly under ice cooling. After stirring at room temperature for 4 hours, the reaction mixture was added with saturated aqueous ammonium chloride solution and then stirred for further 30 minutes. Insoluble matter was removed by filtration through celite, and the filtrate was concentrated under reduced pressure. The residue was purified by column chromatography over silica gel (ethyl acetate:n-hexane=1:1) to obtain Compound 1 (24 mg, 88.2%) as pale brown solids.

mp: 224–226° C.; $^1$H-NMR(CDCl$_3$): δ 3.79(s, 3H), 6.9–7.4(m, 10H), 7.64(d, J=7.8 Hz, 2H), 7.92(br s, 2H). IR(KBr): 3395, 3050, 1510, 1455, 1415, 1340, 1210, 1100, 800, 740 cm$^{-1}$. MS m/z: 311(M$^+$).

Example 2

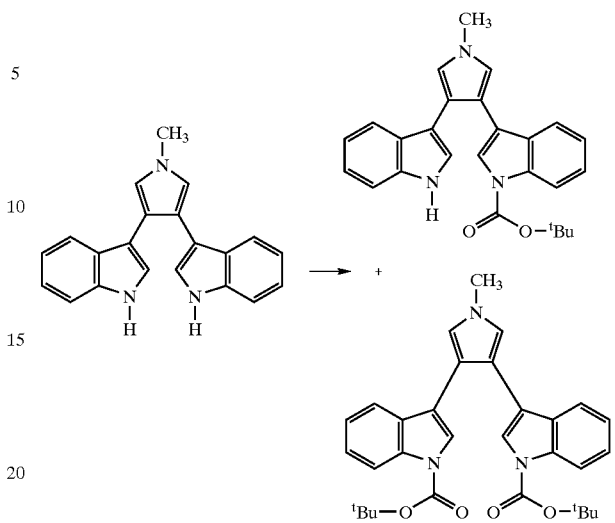

To a solution of Compound 1 (40 mg, 0.13 mmol) dissolved in THF (2 mL) were added di-tert-butyl dicarbonate (28 mg, 0.13 mmol) and dimethylaminopyridine (0.8 mg, 0.0064 mmol) under ice cooling, and the whole was stirred for 4 hour at room temperature. The reaction mixture was concentrated under reduced pressure and the residue was purified by column chromatography over silica gel (ethyl acetate:n-hexane=1:4) to obtain Compound 2 (22 mg, 41.6%) and Compound 3 (31 mg, 47.6%) as pale yellow solids.

Compound 2 mp: 100–102° C.; $^1$H-NMR(CDCl$_3$): δ 1.58(s, 9H), 3.79 (s, 3H), 6.88(d, J=2.3 Hz, 1H), 6.90(d, J=2.3 Hz, 1H), 6.99(d, J=2.3 Hz, 1H), 7.07(t, J=7.5 Hz, 1H), 7.10(t, J=7.9 Hz, 1H), 7.18(t, J=7.9 Hz, 1H), 7.24(t, J=7.9 Hz, 1H), 7.33(d, J=7.9 Hz, 1H), 7.39(bs, 1H), 7.40(d, J=7.9 Hz, 1H), 7.73(d, J=7.9 Hz, 1H), 7.90(brd, J=7.9 Hz, 1H), 8.13(br s, 1H). IR(KBr): 3410, 2945, 1730, 1455, 1370, 1242, 1160, 745 cm$^{-1}$. MS m/z 411(M$^+$).

Compound 3 mp: 85–87° C.; $^1$H-NMR(CDCl$_3$): δ 1.54(s, 18H), 3.78(s, 3H), 6.95(s, 2H), 7.15(t, J=7.5 Hz, 2H), 7.27(t, J=7.5 Hz, 2H), 7.31(bs, 2H), 7.53(d, J=7.5 Hz, 2H), 8.14(brd, J=7.5 Hz, 2H). IR(KBr): 3450, 2970, 1737, 1460, 1375, 1250, 1160, 1060, 750 cm$^{-1}$. MS m/z: 511(M$^+$).

Example 3

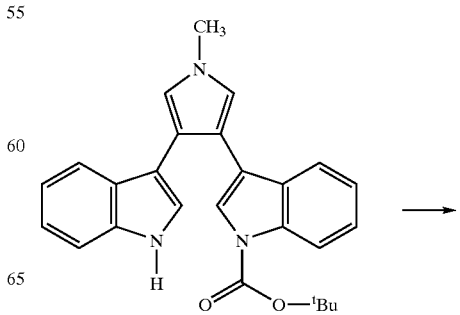

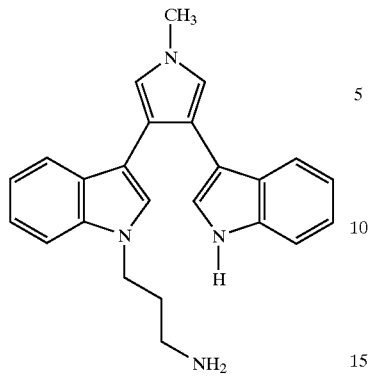

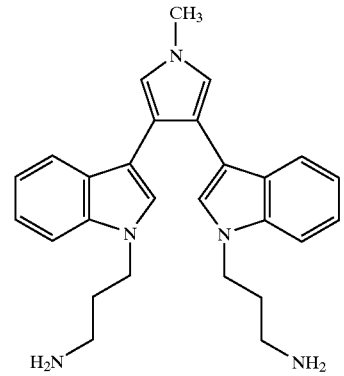

Sodium hydride (60 to 72%, oily, 5.8 mg) was washed with pentane and then suspended into DMF (0.5 mL). A DMF solution (0.5 mL) of Compound 2 (20 mg, 0.05 mmol) was added thereto, and the whole was stirred at room temperature for 45 minutes. On the other hand, DMF (0.5 mL) was added under ice cooling to a mixture of 3-chloropropylamine hydrochloride (6.3 mg, 0.05 mmol) and sodium hydride (60 to 72%, oily, 1.9 mg) washed with pentane, and the whole was stirred for 5 minutes and then warmed to room temperature with standing. The supernatant was added to the solution of sodium salt of Compound 2. The resulting mixture was stirred at 40° C. for 1 hour, and then concentrated under reduced pressure to remove DMF. To the residue were added dichloromethane and saturated aqueous sodium chloride solution, and the organic layer was separated. The water layer was extracted with dichloromethane. The resulting organic layers were combined and dried over sodium sulfate. The residue obtained by removing the solvent under reduced pressure was purified by column chromatography over silica gel (chloroform saturated with ammonia:methanol=10:1) to obtain Compound 4 (3.7 mg, 20.7%) as pale orange solids.

mp: 91–95° C.; $^1$H-NMR(CDCl$_3$): δ 1.43(br s, 2H), 1.76(tt, J=6.8, 6.8 Hz, 2H), 2.43(t, J=6.8 Hz, 2H), 3.79(s, 3H), 4.03(t, J=6.8 Hz, 2H), 6.77(s, 1H), 6.90(s, 1H), 6.94(s, 1H), 6.97(d, J=2.0 Hz, 1H), 7.02(t, J=8.0 Hz, 1H), 7.06(t, J=8.0 Hz, 1H), 7.14(t, J=8.0 Hz, 1H), 7.18(t, J=8.0 Hz, 1H), 7.30(d, J=8.0 Hz, 1H), 7.35(d, J=8.0 Hz, 1H), 7.58(d, J=8.0 Hz, 1H), 7.71(d, J=8.0 Hz, 1H), 8.23(br s, 1H). IR(KBr): 3400, 2940, 1660, 1520, 1460, 1340, 1100, 745 cm$^{-1}$. MS m/z: 368(M$^+$).

Sodium hydride (60 to 72%, oily, 19 mg) was washed with pentane and then suspended into DMF (0.5 mL). A DMF solution (0.5 mL) of Compound 1 (50 mg, 0.16 mmol) was added thereto, and the whole was stirred at room temperature for 45 minutes. On the other hand, DMF (1 mL) was added under ice cooling to a mixture of 3-chloropropylamine hydrochloride (21 mg, 0.16 mmol) and sodium hydride (60 to 72%, oily, 6 mg) washed with pentane, and the whole was stirred for 5 minutes and then warmed to room temperature with standing. The supernatant was added to the solution of sodium salt of Compound 2. The resulting mixture was stirred at 40° C. for 1.5 hour, and then concentrated under reduced pressure to remove DMF. To the residue was added dichloromethane and saturated aqueous sodium chloride solution, and the organic layer was separated. The water layer was extracted with dichloromethane. The resulting organic layers were combined and dried over sodium sulfate. The residue obtained by removing the solvent under reduced pressure was purified by column chromatography over silica gel (chloroform saturated with ammonia:methanol=8:1) to obtain Compound 5 (29 mg, 37.7%) as pale orange solids.

mp: 159–161° C.; $^1$H-NMR(CDCl$_3$): δ 1.44(br s, 4H), 1,79(tt, J=6.8, 6.8 Hz, 4H), 2.48(t, J=6.8 Hz, 4H), 3.77(s, 3H), 4.07(t, J=6.8 Hz, 4H), 6.83(s, 2H), 6.90(s, 2H), 7.02(t, J=8.0 Hz, 2H), 7.17(t, J=8.0 Hz, 2H), 7.31(d, J=8.0 Hz, 2H), 7.62(d, J=8.0 Hz, 2H). IR(KBr): 3425, 2940, 1660, 1620, 1520, 1470, 1390, 745 cm$^{-1}$. MS m/z: 425(M$^+$).

Example 4

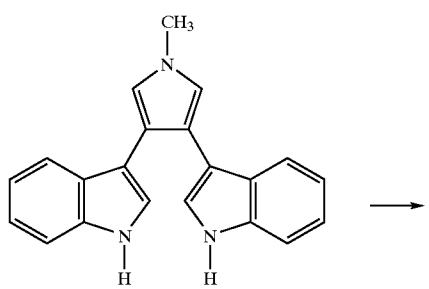

Example 5

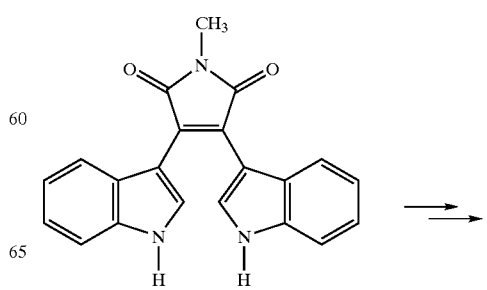

19
-continued

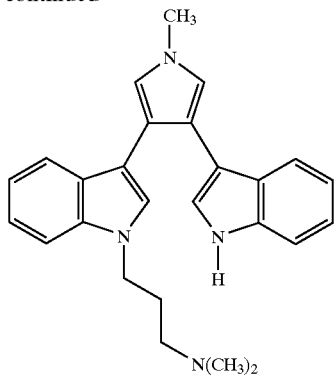

Sodium hydride (60 to 72%, oily, 50 mg) was washed with pentane and then suspended into DMF (0.3 mL). A DMF solution (1.2 mL) of 2,3-bis(1H-indol-3-yl)-N-methylmaleimide (150 mg, 0.44 mmol) synthesized according to a known method (Tetrahedron, Vol. 44, p. 1887, 1988) was added thereto, and the whole was stirred at room temperature for 45 minutes. On the other hand, DMF (1.2 mL) was added at 0° C. to a mixture of (3-chloropropyl) dimethylamine hydrochloride (70 mg, 0.44 mmol) and sodium hydride (60 to 75%, oily, 18 mg) washed with pentane, and the whole was stirred for 5 minutes and then warmed to room temperature with standing. The supernatant was added to the solution of sodium salt of 2,3-bis(1H-indol-3-yl)-N-methylmaleimide. The resulting mixture was stirred at 40° C. for 1.5 hours, and then DMF was removed under reduced pressure. To the residue were added dichloromethane and saturated aqueous sodium chloride solution, and the organic layer was separated. The water layer was further extracted with dichloromethane. The resulting organic layers were combined and dried over sodium sulfate. The residue obtained by removing the solvent under reduced pressure was purified by column chromatography over silica gel (chloroform saturated with ammonia:methanol=10:1) to obtain 2-[1-(3-dimethylaminopropyl)-1H-indol-3-yl]-3-(1H-indol-3-yl)-N-methylmaleimide (77 mg, 41%) as dark red solids.

mp: 86–90° C.; $^1$H-NMR(CDCl$_3$): δ1.95(tt, J=6.8, 6.8 Hz, 2H), 2.21(s, 6H), 2.23(t, J=6.8 Hz, 2H), 3.19(s, 3H), 4.21(t, J=6.8 Hz, 2H), 6.60–6.82(m, 2H), 6.95(d, J=8.1 Hz, 1H), 7.00–7.12(m, 3H), 7.26–7.35(m, 2H), 7.67(s, 1H), 7.72(d, J=2.7 Hz, 1H), 8.60(br s, 1H). IR(KBr): 3395, 2950, 1700, 1535, 1440, 1390, 750 cm$^{-1}$. MS m/z: 426(M$^+$).

To a solution of 2-[1-(3-dimethylaminopropyl)-1H-indol-3-yl]-3-(1H-indol-3-yl)-N-methylmaleimide (60 mg, 0.14 mmol) in MeOH (3 mL) was added a small amount of 10% palladium-carbon, and the whole was stirred at room temperature for 1 day under hydrogen atmosphere. The palladium-carbon was removed by filtration, and the filtrate was concentrated under reduced pressure. The residue was purified by column chromatography over silica gel (dichloromethan:methanol=8:1) to obtain 3-[1-(3-dimethylaminopropyl)-1H-indol-3-yl]-3-(1H-indol-3-yl)-1-methyl-2,5-dioxopyrrolidine (49 mg, 81.5%) as pale red solids.

$^1$H-NMR(CDCl$_3$): δ 1.41–1.55(m, 2H), 1.79–1.92(m, 2H), 2.08(s, 6H), 3.27(s, 3H), 3.65–3.74(m, 1H), 3.75–3.84 (m, 1H), 4.73–4.82(m, 2H), 6.52(s, 1H), 6.64(d, J=2.2 Hz, 1H), 6.89(t, J=7.9 Hz, 1H), 6.95(t, J=7.9 Hz, 1H), 6.97(t, J=7.9 Hz, 1H), 7.01–7.08(m, 3H), 7.17(d, J=7.9 Hz, 1H), 7.28(d, J=7.9 Hz, 1H), 8.57(br s, 1H). MS m/z: 396(M$^+$).

20

To a solution of 3-[1-(3-dimethylaminopropyl)-1H-indol-3-yl]-4-(1H-indol-3-yl)-1-methyl-2,5-dioxopyroridine (49 mg, 0.114 mmol) in THF (5 mL) was added 0.94M diisobutylaluminum hydride (0.49 mL, 0.46 mmol) dropwise slowly under ice cooling. After stirring at room temperature for 4 hours, the reaction mixture was added with saturated aqueous ammonium chloride solution and then stirred for further 30 minutes. Insoluble matter was removed by filtration through celite, and the filtrate was concentrated under reduced pressure. The residue was purified by column chromatography over silica gel (dichloromethan:methanol= 10:1) to obtain Compound 6 (19 mg, 42.6%) as pale brown solids.

mp: 80–83° C.; $^1$H-NMR(CDCl$_3$): δ 1.90(tt, J=7.1, 7.1 Hz, 2H), 2.25(s, 6H), 2.32(t, J=7.1 Hz, 2H), 3.78(s, 3H), 4.01(t, J=7.1 Hz, 2H), 6.76(s, 1H), 6.89–6.96(m, 3H), 7.02(t, J=8.0 Hz, 1H), 7.08(t, J=8.0 Hz, 1H), 7.13(t, J=8.0 Hz 1H), 7.18(t, J=8.0 Hz, 1H), 7.28(d, J=8.0 Hz, 1H), 7.34(d, J =8.0 Hz, 1H), 7.62(d, J=8.0 Hz, 1H), 7.71(d, J=8.0 Hz, 1H), 8.67(br s, 1H). IR(KBr): 3400, 2950, 1515, 1470, 1460, 1340, 1240, 1215, 740 cm$^{-1}$. MS m/z: 396(M$^+$).

Example 6

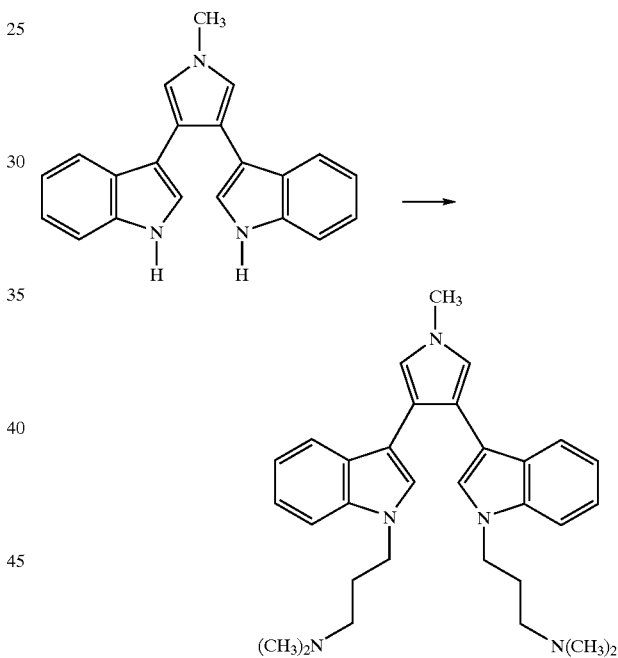

Sodium hydride (60 to 72%, oily, 5.8 mg) was washed with pentane and then suspended into DMF (1 mL). A DMF solution (2 mL) of Compound 1 (15 mg, 0.048 mmol) was added thereto, and the whole was stirred at room temperature for 45 minutes. On the other hand, DMF (1 mL) was added under ice cooling to a mixture of (3-chloropropyl) dimethylamine hydrochloride (17 mg, 0.11 mmol) and sodium hydride (60 to 72%, oily, 4.2 mg) washed with pentane, and the whole was stirred for 5 minutes and then warmed to room temperature with standing. The supernatant was added to the solution of sodium salt of Compound 1. The resulting mixture was stirred at 40° C. for 1.5 hour, and then concentrated under reduced pressure to remove DMF. To the residue were added dichloromethane and saturated aqueous sodium chloride solution, and the organic layer was separated. The water layer was extracted with dichloromethane. The resulting organic layers were combined and dried over sodium sulfate. The residue obtained by removing the solvent under reduced pressure was purified by column chromatography over silica gel (chloroform saturated with ammonia:methanol=10:1) to obtain Compound 7 (8.5 mg, 36.6%) as pale orange oil.

$^1$H-NMR(CDCl$_3$): δ 1.81(tt, J=6.9, 6.9 Hz, 4H), 2.13(s, 12H), 2.14(t, J=6.9 Hz, 4H), 3.78(s, 3H), 4.05(t, J=6.9 Hz, 4H), 6.84(s, 2H), 6.90(s, 2H), 7.01(t, J=7.8 Hz, 2H), 7.16(t, J=7.8 Hz, 2H), 7.32(d, J=7.8 Hz, 2H), 7.61(d, J=7.8 Hz, 2H). IR(KBr): 3450, 2950, 1520, 1470, 1160, 740 cm$^{-1}$. MS m/z: 481(M$^+$).

Example 7

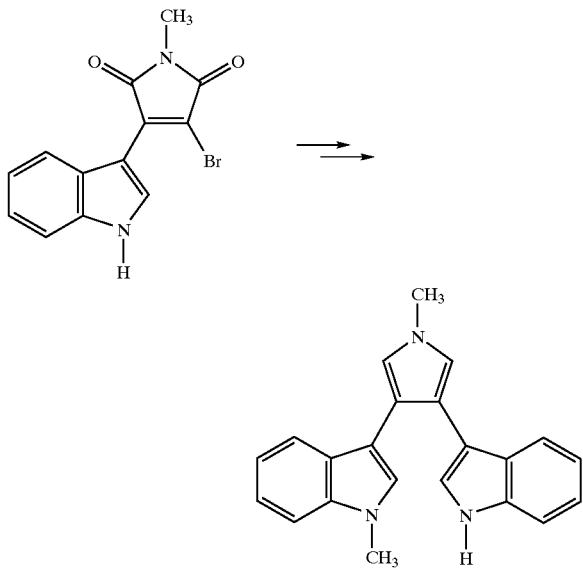

Potassium carbonate (140 mg, 0.98 mmol) and methyl iodide (0.06 mL, 0.98 mmol) were added under ice cooling to 2-bromo-3-(1H-indol-3-yl)-N-methylmaleimide (100 mg, 0.33 mmol) synthesized according to a known method (Tetrahedron, Vol. 44, p. 2887, 1988) and dissolved in DMF (5 mL), and the whole was stirred for 2 hours. The reaction mixture was warmed to room temperature, added with saturated aqueous sodium chloride solution, and extracted with ethyl acetate. The extract was dried over sodium sulfate, and then concentrated under reduced pressure. The residue was purified by column chromatography over silica gel (ethyl acetate:n-hexane=1:1) to obtain 2-bromo-3-(1-methyl-1H-indol-3-yl)-N-methylmaleimide (99 mg, 95.1%) as red solids.

mp: 155–158° C.; $^1$H-NMR(CDCl$_3$): δ 3.17(s, 3H), 3.89 (s, 3H), 7.16–7.41(m, 4H), 8.05–8.11(m, 1H). IR(KBr): 1760, 1700, 1585, 1510, 1430, 1375, 1230, 1150, 1120, 980, 800, 730 cm$^{-1}$. MS m/z: 318(M$^+$).

To a solution of indole (66 mg, 0.21 mmol) dissolved in toluene (1 mL) was added 0.95M ethylmagnesium bromide (0.5 mL, 0.47 mmol) at 40 ° C., and the whole was stirred at 40° C. for 45 minutes. Successively, a solution of 2-bromo-3-(1-methyl-1H-indol-3-yl)-N-methylmaleimide (66 mg, 0.21 mmol) dissolved in toluene (3 mL) was added thereto, followed by stirring under heating and refluxing for 2 hours. After 20% aqueous citric acid solution (1 mL) was added thereto under ice cooling and the whole was stirred, toluene was removed by concentration under reduced pressure and the resulting concentrate was extracted with ethyl acetate. The extract was dried over sodium sulfate and then concentrated under reduced pressure. The residue was purified by column chromatography over silica gel (ethyl acetate:n-hexane=1:1) to obtain 3-(1H-indol-3-yl)-2-(1-methyl-1H-indol-3-yl)-N-methylmaleimide (71 mg, 96.8%) as red solids.

mp: 168–171° C.; $^1$H-NMR(DMSO-d$_6$): δ 3.05(s, 3H), 3.35(s, 3H), 6.65(t, J=8.0 Hz, 2H), 6.75(d, J=8.0 Hz, 1H), 6.85(d, J=8.0 Hz, 1H), 6.98(t, J=8.0 Hz, 1H), 7.03(t, J=8.0 Hz, 1H), 7.38(d, J=8.0 Hz, 1H), 7.42(d, J=8.0 Hz, 1H), 7.74(d, 2.8 Hz, 1H), 7.82(s, 1H), 11.66(br s, 1H). IR(KBr): 3450, 1700, 1540, 1440, 1380 cm$^{-1}$. MS m/z: 355(M$^+$).

To a solution of 3-(1H-indol-3-yl)-2-(1-methyl-1H-indol-3-yl)-N-methylmaleimide (60 mg, 0.17 mmol) in DMF (1 mL) was added a small amount of 10% palladium-carbon, and the whole was stirred at room temperature for 1 day under hydrogen atmosphere. The palladium-carbon was removed by filtration, and the filtrate was concentrated under reduced pressure. The residue was purified by column chromatography over silica gel (ethyl acetate:n-hexane= 2:1) to obtain 4-(1H-indol-3-yl)-3-(1-methyl-1H-indol-3-yl)-1-methyl-2,5-dioxopyrrolidine (60 mg, 99.6%) as pale red solids. $^1$H-NMR(CDCl$_3$): δ 3.27(s, 3H), 3.34(s, 3H), 4.76(s, 2H) 6.58–7.32(m, 10H), 7.72(br s, 1H).

To a solution of 4-(1H-indol-3-yl)-3-(1-methyl-1H-indol-3-yl)-1-methyl-2,5-dioxopyrrolidine (60 mg, 0.17 mmol) in THF (3 mL) was added 0.94M diisobutylaluminum hydride (0.7 mL, 0.67 mmol) dropwise slowly under ice cooling. After stirring at room temperature for 4 hours, the reaction mixture was added with saturated aqueous ammonium chloride solution and then stirred for further 30 minutes. Insoluble matter was removed by filtration through celite, and the filtrate was concentrated under reduced pressure. The residue was purified by column chromatography over silica gel (ethyl acetate:n-hexane=1:1) to obtain Compound 8 (37 mg, 64.9%) as colorless solids.

mp: 83–88° C.; $^1$H-NMR(CDCl$_3$): δ 3.57(s, 3H), 3.70(s, 3H), 6.74(s, 1H), 6.82–7.37(m, 9H), 7.52(d, J=7.9 Hz, 1H), 7.64(d, J=7.9 Hz, 1H), 7.80(br s, 1H). IR(KBr): 3400, 2925, 1510, 1480, 1460, 1420, 1330, 1225, 740 cm$^{-1}$. MS m/z: 325(M$^+$).

Example 8

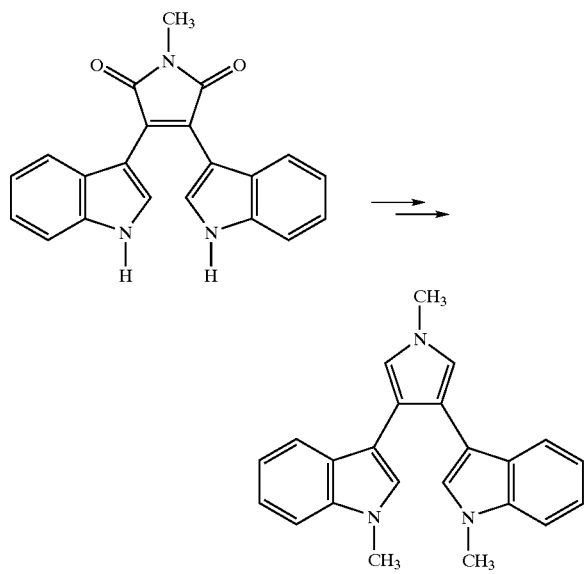

2,3-bis(1H-indol-3-yl)-N-methylmaleimide (50 mg, 0.15 mmol) synthesized according to a known method (Tetrahedron, Vol. 44, p. 2887, 1988) was dissolved in DMF (2 mL), and potassium carbonate (120 mg, 0.88 mmol) and methyl iodide (0.05 mL, 0.88 mmol) were added thereto under ice cooling. The whole was stirred for 19 hours. The reaction mixture was warmed to room temperature, added with saturated aqueous sodium chloride solution, and extracted with ethyl acetate. The extract was dried over sodium sulfate, and then concentrated under reduced pressure. The residue was purified by column chromatography over silica gel (ethyl acetate:n-hexane=1:1) to obtain 2,3-bis(1-methyl-1H-indol-3-yl)-N-methylmaleimide (54 mg, 99.4%) as red solids.

mp: >290° C.; $^1$H-NMR(CDCl$_3$): δ 3.17(s, 3H), 3.82(s, 6H), 6.72(t, J=8.1 Hz, 2H), 6.91(d, J=8.1 Hz, 2H), 7.09(t, J=8.1 Hz, 2H), 7.27(d, J=8.1 Hz, 2H), 7.67(s, 2H). IR(KBr): 3390, 1695, 1530, 1440, 1385, 740 cm$^{-1}$ MS m/z: 369(M$^+$).

To a solution of 2,3-bis(1-methyl-1H-indol-3-yl)-N-methylmaleimide (50 mg, 0.14 mmol) in DMF (1 mL) was added a small amount of 10% palladium-carbon, and the whole was stirred at room temperature for 1 day under hydrogen atmosphere. The palladium-carbon was removed by filtration, and the filtrate was concentrated under reduced pressure. The residue was purified by column chromatography over silica gel (ethyl acetate:n-hexane=2:1) to obtain 1-methyl-3,4-bis(1-methyl-1H-indol-3-yl)-2,5-dioxopyrrolidine (28 mg, 55.7%) as pale red solids. $^1$H-NMR(CDCl$_3$): δ 3.28(s, 3H), 3.44(s, 6H), 4.81(s, 2H), 6.63(s, 2H), 6.85–7.00(m, 2H), 7.04–7.11(m, 4H), 7.22–7.26(m, 2H).

To a solution of 1-methyl-3,4-bis(1-methyl-1H-indol-3-yl)-2,5-dioxopyrrolidine (20 mg, 0.054 mmol) in THF (1 mL) was added 0.94M diisobutylaluminum hydride (0.2 mL, 0.22 mmol) dropwise slowly under ice cooling. After stirring at room temperature for 4 hours, the reaction mixture was added with saturated aqueous ammonium chloride solution and then stirred for further 30 minutes. Insoluble matter was removed by filtration through celite, and the filtrate was concentrated under reduced pressure. The residue was purified by column chromatography over silica gel (ethyl acetate:n-hexane=1:1) to obtain Compound 9 (15 mg, 79.3%) as colorless solids.

mp: 169–173° C.; $^1$H-NMR(CDCl$_3$): δ 3.66(s, 6H), 3.78 (s, 3H), 6.81(s, 2H) 6.90(s, 2H), 7.06(t, J=7.8 Hz, 2H), 7.20(t, J=7.8 Hz, 2H), 7.29(d, J=7.8 Hz, 2H), 7.66(d. J=7.8 Hz, 2H). IR(KBr): 3450, 2940, 1515, 1480, 1420, 1330, 1260, 1240, 800, 740 cm$^{-1}$. MS m/z: 339(M$^+$).

Example 9

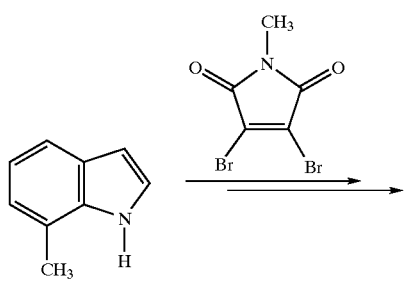

-continued

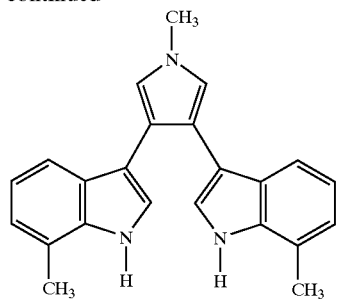

To a solution of 7-methylindole (162 mg, 1.23 mmol) dissolved in toluene (4 mL) was added 0.96M ethylmagnesium bromide (1.28 mL, 1.23 mmol) at 40° C., and the whole was stirred at 40° C. for 45 minutes. Successively, thereto was added a solution of 2,3-dibromomaleimide (70.4 mg, 0.276 mmol) dissolved in toluene (9 mL), followed by stirring under heating and refluxing for 2 hours. After 20% aqueous citric acid solution (0.5 mL) was added thereto under ice cooling and the whole was stirred, toluene was removed by concentration under reduced pressure and the resulting concentrate was extracted with dichloromethane. The extract was dried over magnesium sulfate and then concentrated under reduced pressure. The residue was purified by column chromatography over silica gel (ethyl acetate:n-hexane=1:5 to 1:1) to obtain N-methly-2,3-bis(7-methyl-1H-indol-3-yl)maleimide (99 mg, 97%) as red solids.

mp: >300° C.; $^1$H-NMR(CDCl$_3$): δ 2.48(s, 6H), 3.21(s, 3H), 6.6–7.0(m, 6H), 7.75(d, J=3.0 Hz, 2H), 8.43(br s, 2H). IR(KBr): 3320, 1680, 1530, 1420, 1370, 1110, 800, 750, 670, 590 cm$^{-1}$. MS m/z 369(M$^+$).

Lithium aluminum hydride (53 mg, 1.39 mmol) was added to a stirred solution of N-methyl-2,3-bis(7-methyl-1H-indol-3-yl)maleimide (78 mg, 0.211 mmol) in THF (9 mL). The mixture was stirred at room temperature for 18 hours. The mixture was quenched with water (3.5 mL), and then acidified to pH2 with 2N HCl and extracted with dichloromethane. The extract was dried over magnesium sulfate and then concentrated under reduced pressure. The residue was purified by column chromatography over silica gel (ethyl acetate:n-hexane=1:10–1:5) to obtain Compound 10 (14 mg, 20%) as pale green solids.

mp: 249–254° C.; $^1$H-NMR(CDCl$_3$): δ 2.46(s, 6H), 3.78 (s, 3H), 6.80–7.01(m, 8H), 7.40–7.55(m, 2H), 7.80(br s, 2H). IR(KBr): 3450, 3380, 1500, 1450, 1430, 1340, 1220, 1180, 800, 750 cm$^{-1}$. MS m/z: 339(M$^+$).

Example 10

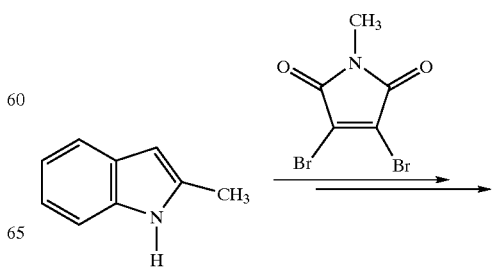

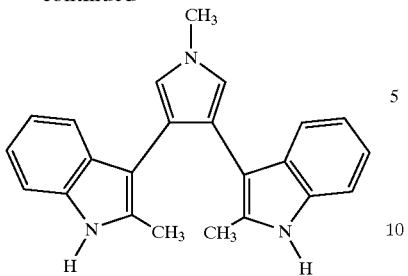

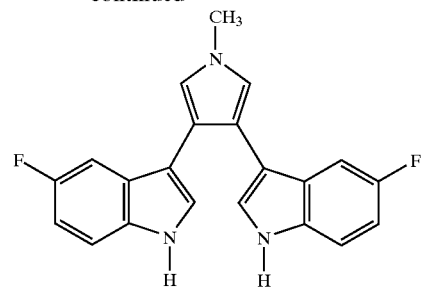

To a solution of 2-methylindole (1.0 g, 8.82 mmol) dissolved in THF (10 mL) was added 0.95M ethylmagnesium bromide (9.3 mL, 8.82 mmol) at 40° C., and the whole was stirred at 40° C. for 45 minutes. Successively, a solution of 2,3-dibromomaleimide (500 mg, 1.96 mmol) dissolved in THF (4 mL) was added thereto, followed by stirring under heating and refluxing for 3 hours. After addition of 20% aqueous citric acid solution (9 mL) to the reaction mixture under ice cooling and successive stirring, THF was removed by concentration under reduced pressure and the resulting concentrate was extracted with ethyl acetate. The extract was dried over sodium sulfate and then concentrated under reduced pressure. The residue was purified by column chromatography over silica gel (ethyl acetate:n-hexane=1:2) to obtain N-methyl-2,3-bis(2-methyl-1H-indol-3-yl)maleimide (452 mg, 62.4%) as red solids.

mp: >290° C.; $^1$H-NMR(CDCl$_3$): δ 2.06(s, 6H), 3.22(s, 3H), 6.92(t, J=7.6 Hz, 2H), 7.08(t, J=7.6 Hz, 2H), 7.15–7.24 (m, 4H), 8.04(br s, 2H). IR(KBr)3380, 3310, 1705, 1460, 1440, 1380 cm$^{-1}$. MS m/z: 369(M$^+$).

To a solution of N-methyl-2,3-bis(2-methyl-1H-indol-3-yl)maleimide (50 mg, 0.14 mmol) in THF (2 mL) was added 0.94M diisobutylaluminum hydride (0.58 mL, 0.54 mmol) dropwise slowly under ice cooling. After stirring at room temperature for 4 hours, the reaction mixture was added with saturated aqueous ammonium chloride solution and then stirred for further 30 minutes. Insoluble matter was removed by filtration through celite, and the filtrate was concentrated under reduced pressure. The residue was purified by column chromatography over silica gel (ethyl acetate:n-hexane=2:1) to obtain Compound 11 (20 mg, 40.7%) as colorless solids.

mp: 134–136° C.; $^1$H-NMR(CDCl$_3$): δ 1.85(s, 6H), 3.83 (s, 3H), 6.86(s, 2H), 6.97(t, J=7.9 Hz, 2H), 7.06(t, J=7.9 Hz, 2H), 7.21(d, J=7.9 Hz, 2H), 7.50(d, J=7.9 Hz, 2H), 7.66(br s, 2H). IR(KBr)3405, 2925, 1465, 1420, 1310, 1290, 1210, 1170, 750 cm$^{-1}$. MS m/z: 339(M$^+$).

Example 11

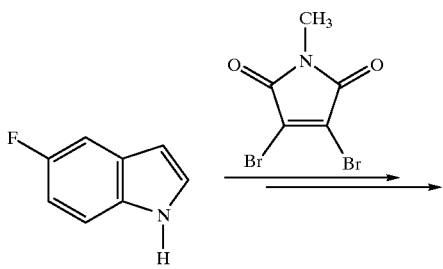

To a solution of 5-fluoroindole (240 mg, 1.77 mmol) dissolved in toluene (4 mL) was added 1.02M ethylmagnesium bromide (1.7 mL, 1.77 mmol) at 40° C., and the whole was stirred at 40° C. for 45 minutes. Successively, a solution of 2,3-dibromomaleimide (100 mg, 0.4 mmol) dissolved in toluene (6 mL) was added thereto, followed by stirring under heating and refluxing for 3 hours. After addition of 20% aqueous citric acid solution (2 mL) to the reaction mixture under ice cooling and successive stirring, toluene was removed by concentration under reduced pressure and the resulting concentrate was extracted with ethyl acetate. The extract was dried over sodium sulfate and then concentrated under reduced pressure. The residue was purified by column chromatography over silica gel (ethyl acetate:n-hexane=1:1) to obtain 2,3-bis(5-fluoro-1H-indol-3-yl)-N-methylmaleimide (125 mg, 84.8%) as red solids.

mp: >290° C.; $^1$H-NMR(DMSO-d$_6$): δ 3.03(s, 3H), 6.38 (dd, J=9.0, 2.5 Hz, 2H), 6.83(dt, J=2.5, 9.0 Hz, 2H), 7.39(dd, J=9.0, 4.6 Hz, 2H), 7.89(m, 2H), 11.83(br s, 2H). IR(KBr): 3440, 3350, 1700, 1530, 1450, 1430 cm$^{-1}$. MS m/z: 377 (M$^+$).

To a solution of 2,3-bis(5-fluoro-1H-indol-3-yl)-N-methylmaleimide (60 mg, 0.16 mmol) in DMF (3 mL) was added a small amount of 10% palladium-carbon, and the whole was stirred at room temperature for 1 day under hydrogen atmosphere. The palladium-carbon was removed by filtration, and the filtrate was concentrated under reduced pressure. The residue was purified by column chromatography over silica gel (ethyl acetate:n-hexane=2:1) to obtain 3,4-bis(5-fluoro-1H-indol-3-yl)-1-methyl-2,5-dioxopyrrolidine (58.8 mg, 97.5%) as pale red solids. $^1$H-NMR(CDCl$_3$): δ 3.11(s, 3H), 4.90(s, 2H), 6.74(dt, J=2.5, 9.0 Hz, 2H), 6.99(d, J=2.5 Hz, 2H), 7.01(dd, J=9.0, 2.5 Hz, 2H), 7.09(dd, J=9.0,4.6 Hz, 2H), 10.77(br s, 2H). IR(KBr): 3420, 1700, 1490, 1440, 1295, 940, 800 cm$^{-1}$. MS m/z: 379(M$^+$).

To a solution of 3,4-bis(5-fluoro-1H-indol-3-yl)-1-methyl-2,5-dioxopyrrolidine (50 mg, 0.13 mmol) in THF (3 mL) was added 0.94M diisobutylaluminum hydride (0.56 mL, 0.53 mmol) dropwise slowly under ice cooling. After stirring at room temperature for 4 hours, the reaction mixture was added with saturated aqueous ammonium chloride solution and then stirred for further 30 minutes. Insoluble matter was removed by filtration through celite, and the filtrate was concentrated under reduced pressure. The residue was purified by column chromatography over silica gel (ethyl acetate:n-hexane=1:2) to obtain Compound 12 (35 mg, 77.4%) as colorless solids.

mp: 94–97° C.; $^1$H-NMR(CDCl$_3$): δ 3.77(s, 3H), 6.87(s, 2H), 6.89–6.99(m, 4H), 7.19–7.30(m, 4H), 7.90(br s, 2H). IR(KBr): 3410, 2925, 1580, 1480, 1455, 1420, 1170, 800 cm$^{-1}$. MS m/z: 347(M$^+$).

Example 12

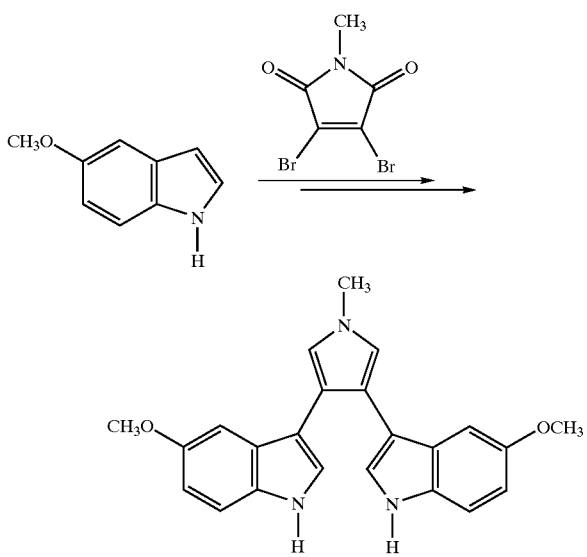

To a solution of 5-methoxyindole (520 mg, 3.53 mmol) dissolved in toluene (8 mL) was added 0.95M ethylmagnesium bromide (3.7 mL, 3.53 mmol) at 40° C., and the whole was stirred at 40° C. for 45 minutes. Successively, a solution of 2,3-dibromomaleimide (200 mg, 0.73 mmol) dissolved in toluene (12 mL) was added thereto, followed by stirring under heating and refluxing for 3 hours. After addition of 20% aqueous citric acid solution (2 mL) to the reaction mixture under ice cooling and successive stirring, toluene was removed by concentration under reduced pressure and the resulting concentrate was extracted with ethyl acetate. The extract was dried over sodium sulfate and then concentrated under reduced pressure. The residue was purified by column chromatography over silica gel (ethyl acetate:n-hexane=1:1) to obtain 2,3-bis(5-methoxy-1H-indol-3-yl)-N-methylmaleimide (136 mg, 86.4%) as red solids.

mp: >290° C.; $^1$H-NMR(DMSO-$d_6$): δ 3.03(s, 3H), 3.33 (s, 6H), 6.21(d, J=2.3 Hz, 2H), 6.55(dd, J=8.7, 2.3 Hz, 2H), 7.23(d, J=8.7 Hz, 2H), 7.77(d, J=2.8 Hz, 2H), 11.55(br s, 1H), 11.56(br s, 1H). IR(KBr): 3325, 1690, 1530, 1460, 1440, 1220, 1165, 805 cm$^{-1}$. MS m/z: 401(M$^+$).

To a solution of 2,3-bis(5-methoxy-1H-indol-3-yl)-N-methylmaleimide (100 mg, 0.25 mmol) in DMF (5 mL) was added a small amount of 10% palladium-carbon, and the whole was stirred at room temperature for 1 day under hydrogen atmosphere. The palladium-carbon was removed by filtration, and the filtrate was concentrated under reduced pressure. The residue was purified by column chromatography over silica gel (ethyl acetate:n-hexane=2:1) to obtain 3,4-bis(5-methoxy-1H-indol-3-yl)-1-methyl-2,5-dioxopyrrolidine (20 mg, 19.9%) as a mixture of two isomers (A:B=2:1) as pale red solids.

A] $^1$H-NMR(CDCl$_3$): δ 3.59(s, 3H), 3.66(s, 6H), 4.72(s, 2H), 6.50–7.21(m, 8H), 7.80(br s, 2H). B] $^1$H-NMR (CDCl$_3$): δ 3.23(s, 3H), 3.26(s, 6H), 4.37(s, 2H), 6.50–7.21 (m, 8H), 8.26(br s, 2H).

To a solution of 3,4-bis(5-methoxy-1H-indol-3-yl)-1-methyl-2,5-dioxopyrrolidine (20 mg, 0.05 mmol) in THF (2 mL) was added 0.94M diisobutylaluminum hydride (0.2 mL, 0.2 mmol) dropwise slowly under ice cooling. After stirring at room temperature for 4 hours, the reaction mixture was added with saturated aqueous ammonium chloride solution and then stirred for further 30 minutes. Insoluble matter was removed by filtration through celite, and the filtrate was concentrated under reduced pressure. The residue was purified by column chromatography over silica gel (ethyl acetate:n-hexane=1:2) to obtain Compound 13 (10 mg, 54.3%) as pale brown solids.

mp: 236–241° C.; $^1$H-NMR(CDCl$_3$): δ 3.55(s, 6H), 3.80 (s, 3H), 6.78(dd, J=8.7, 2.4 Hz, 2H), 6.90(s, 2H), 6.92(d, J=2.4 Hz, 2H), 6.95(d, J=2.4 Hz, 2H), 7.19(d, J=8.7 Hz, 2H), 7.82(br s, 2H). IR(KBr): 3400, 2940, 1480, 1440, 1260, 1220, 1180, 1090, 1030, 855, 810, 790 cm$^{-1}$. MS m/z 371(M$^+$).

Example 13

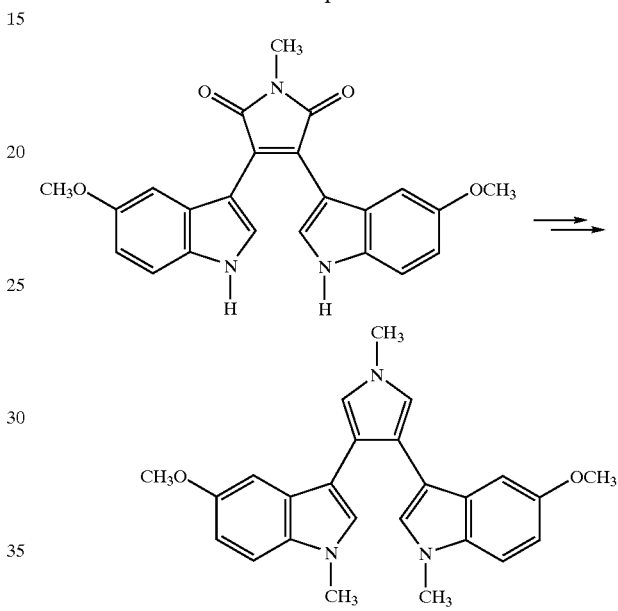

Potassium carbonate (200 mg, 1.5 mmol) and methyl iodide (0.09 mL, 1.5 mmol) were added under ice cooling to 2,3-bis(5-methoxy-1H-indol-3-yl)-N-methylmaleimide (100 mg, 0.25 mmol) dissolved in DMF (5 mL), and the whole was stirred for 1 hours. The reaction mixture was warmed to room temperature, added with saturated aqueous sodium chloride solution, and extracted with ethyl acetate. The extract was dried over sodium sulfate, and then concentrated under reduced pressure. The residue was purified by column chromatography over silica gel (ethyl acetate:n-hexane=1:1) to obtain 2,3-bis(5-methoxy-1-methyl-1H-indol-3-yl)-N-methylmaleimide (90 mg, 84.1%) as red solids.

mp: 114–117° C.; $^1$H-NMR(CDCl$_3$): δ 3.16(s, 6H), 3.18 (s, 3H), 3.79(s, 6H) 6.33(d, J=2.4 Hz, 2H), 6.71(dd, J=8.8, 2.4 Hz, 2H), 7.12(d, J=8.8 Hz, 2H), 7.67(s, 2H). IR(KBr): 3400, 2920, 1700, 1440, 1390, 1295, 1110, 800 cm$^{-1}$. MS m/z 429(M$^+$).

To a solution of 2,3-bis(5-methoxy-1-methyl-1H-indol-3-yl)-N-methylmaleimide (70 mg, 0.16 mmol) in DMF (2 mL) was added a small amount of 10% palladium-carbon, and the whole was stirred at room temperature for 1 day under hydrogen atmosphere. The palladium-carbon was removed by filtration, and the filtrate was concentrated under reduced pressure. The residue was purified by column chromatography over silica gel (ethyl acetate:n-hexane=2:1) to obtain 3,4-bis(5-methoxy-1-methyl-1H-indol-3-yl)-1-methyl-2,5-dioxopyrrolidine (42 mg, 60.4%) as pale red solids.

¹H-NMR(CDCl₃): δ 3.28(s, 3H), 3.44(s, 6H), 3.65(s, 6H) 4.75(s, 2H), 6.52(s, 2H), 6.62(d, J=2.3 Hz, 2H), 6.72(dd, J=8.8, 2.3 Hz, 2H), 6.96(d, J=8.8 Hz, 2H).

To a solution of 3,4-bis(5-methoxy-1-methyl-1H-indol-3-yl)-1-methyl-2,5-dioxopyrrolidine (20 mg, 0.046 mmol) in THF (2 mL) was added 0.94M diisobutylaluminum hydride (0.2 mL, 0.19 mmol) dropwise slowly under ice cooling. After stirring at room temperature for 4 hours, the reaction mixture was added with saturated aqueous ammonium chloride solution and then stirred for further 30 minutes. Insoluble matter was removed by filtration through celite, and the filtrate was concentrated under reduced pressure. The residue was purified by column chromatography over silica gel (ethyl acetate:n-hexane=2:1) to obtain Compound 14 (13 mg, 70.2%) as pale brown solids.

mp: 92–96° C.; ¹H-NMR(CDCl₃): δ 3.57(s, 6H), 3.63(s, 6H), 3.79(s, 3H), 6.80(s, 2H), 6.81(dd, J=8.8, 2.4 Hz, 2H), 6.86(s, 2H), 6.95(d, J=2.4 Hz, 2H), 7.14(d, J=8.8 Hz, 2H). IR(KBr): 3450, 2930, 1490, 1455, 1420, 1220, 1180, 795 cm⁻¹. MS m/z 399(M⁺).

Example 14

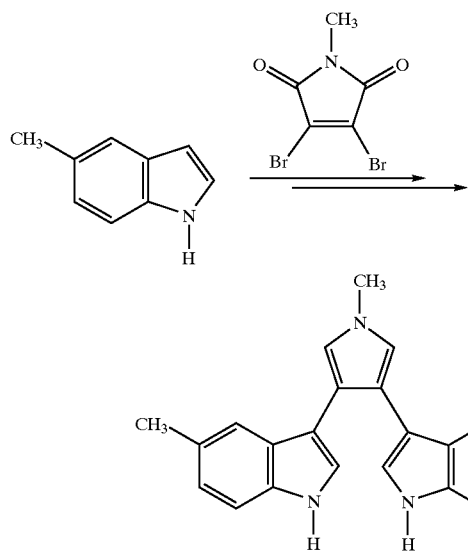

To a solution of 5-methylindole (320 mg, 2.75 mmol) dissolved in toluene (5 mL) was added 0.95M ethylmagnesium bromide (2.8 mL, 2.75 mmol) at 40° C., and the whole was stirred at 40° C. for 45 minutes. Successively, a solution of 2,3-dibromo-N-methylmaleimide (150 mg, 0.61 mmol) dissolved in toluene (3 mL) was added thereto, followed by stirring under heating and refluxing for 3 hours. After addition of 20% aqueous citric acid solution (3 mL) to the reaction mixture under ice cooling and successive stirring, toluene was removed by concentration under reduced pressure and the resulting concentrate was extracted with ethyl acetate. The extract was dried over sodium sulfate and then concentrated under reduced pressure. The residue was purified by column chromatography over silica gel (ethyl acetate:n-hexane=1:1) to obtain N-methyl-2,3-bis(5-methyl-1H-indol-3-yl)maleimide (200 mg, 92.1%) as red solids.

mp: 270–275° C.; ¹H-NMR(CDCl₃): δ 2.06 (s, 6H), 3.20(s, 3H), 6.73(s, 2H), 6.90(d, J=8.3 Hz, 2H), 7.20(d, J=8.3 Hz, 2H), 7.62(d, J=2.8 Hz, 2H), 8.42(br s, 2H). IR(KBr): 3310, 1690, 1525, 1440, 1390, 1160, 1105, 800 cm⁻¹. MS m/z 369(M⁺).

To a solution of N-methyl-2,3-bis(5-methyl-1H-indol-3-yl)maleimide (150 mg, 0.41 mmol) in DMF (3 mL) was added a small amount of 10% palladium-carbon, and the whole was stirred at room temperature for 1 day under hydrogen atmosphere. The palladium-carbon was removed by filtration, and the filtrate was concentrated under reduced pressure. The residue was purified by column chromatography over silica gel (ethyl acetate:n-hexane=2:1) to obtain 1-methyl-3,4-bis(5-methyl-1H-indol-3-yl)-2,5-dioxopyrrolodine (109 mg, 72.4%) as a mixture of two isomers (A:B=3:1) as pale red solids.

A] ¹H-NMR(CDCl₃): δ 2.33(s, 6H), 3.28(s, 3H), 4.75(s, 2H), 6.40–7.35(m, 8H), 7.60(br s, 2H). B] ¹H-NMR (CDCl₃): δ 2.37(s, 6H), 3.28(s, 3H), 4.38(s, 2H), 6.40–7.35 (m, 8H), 8.02(br s, 2H). IR(KBr): 3405, 1700, 1440,1385 cm⁻¹.

To a solution of 1-methyl-3,4-bis(5-methyl-1H-indol-3-yl)-2,5-dioxopyrrolidine (40 mg, 0.27 mmol) in THF (2 mL) was added 0.94M diisobutylaluminum hydride (1.1 mL, 1.08 mmol) dropwise slowly under ice cooling. After stirring at room temperature for 4 hours, the reaction mixture was added with saturated aqueous ammonium chloride solution and then stirred for further 30 minutes. Insoluble matter was removed by filtration through celite, and the filtrate was concentrated under reduced pressure. The residue was purified by column chromatography over silica gel (ethyl acetate:n-hexane=1:1) to obtain Compound 15 (27 mg, 74.1%) as colorless solids.

mp:144–146° C.; ¹H-NMR(CDCl₃): δ 2.39(s, 6H), 3.80(s, 3H), 6.86(d, J=2.4 Hz, 2H), 6.92(s, 2H), 6.99(d, J=8.2 Hz, 2H), 7.21(d, J=8.2 Hz, 2H), 7.45(s, 2H), 7.78(br s, 2H). IR(KBr): 3410, 2925, 1520, 1480, 1460, 1420, 1180, 1000, 800 cm⁻¹. MS m/z 339(M⁺).

Example 15

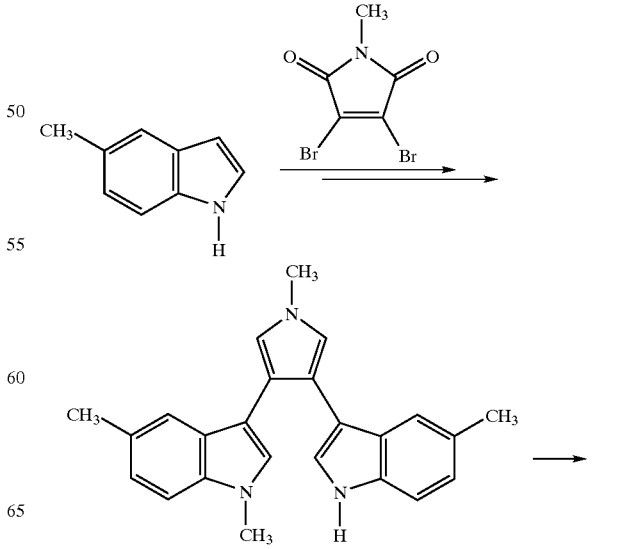

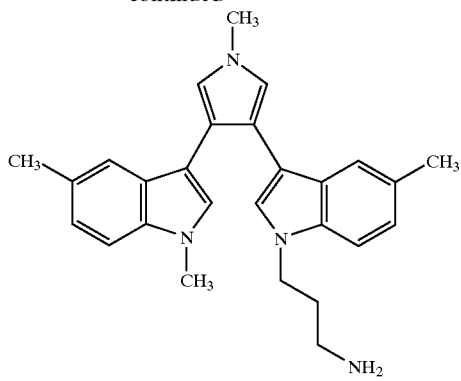

To a solution of 5-methylindole (90 mg, 0.78 mmol) dissolved in THF (3 mL) was added 0.95M ethylmagnesium bromide (0.83 mL, 0.78 mmol) at 40° C., and the whole was stirred at 40° C. for 45 minutes. Successively, thereto was added a solution of 2,3-dibromo-N-methylmaleimide (100 mg, 0.39 mmol) dissolved in THF (5 mL), followed by stirring under heating and refluxing for 3 hours. After 20% aqueous citric acid solution (1 mL) was added thereto under ice cooling and the whole was stirred, THF was removed by concentration under reduced pressure and the resulting concentrate was extracted with ethyl acetate. The extract was dried over sodium sulfate and then concentrated under reduced pressure. The residue was purified by column chromatography over silica gel (ethyl acetate:n-hexane=1:1) to obtain 2-bromo-3-(5-methyl-1H-indol-3-yl)-N-methylmaleimide (108 mg, 86.3%) as red solids.

mp:158–159° C.; $^1$H-NMR(CDCl$_3$): δ 2.49(s, 3H), 3.17(s, 3H), 7.12(d, J=8.2 Hz, 1H), 7.32(d, J=8.2 Hz, 1H), 7.83(s, 1H), 7.94(d, J=3.1 Hz, 1H), 8.81(br s, 1H). IR(KBr): 3275, 1690, 1590, 1240, 1385, 1150, 1090, 800, 725, 600 cm$^{-1}$. MS m/z 318(M$^+$).

Potassium carbonate (130 mg, 0.94 mmol) and methyl iodide (0.06 mL, 0.94 mmol) were added under ice cooling to 2-bromo-3-(5-methyl-1H-indol-3-yl)-N-methylmaleimide (100 mg, 0.31 mmol) dissolved in DMF (5 mL), and the whole was stirred for 1.5 hours. The reaction mixture was warmed to room temperature, added with saturated aqueous sodium chloride solution, and extracted with ethyl acetate. The extract was dried over sodium sulfate, and then concentrated under reduced pressure. The residue was purified by column chromatography over silica gel (ethyl acetate:n-hexane=1:2) to obtain 2-bromo-3-(1,5-dimethyl-1H-indol-3-yl)-N-methylmaleimide (100 mg, 95.8%) as red solids.

mp:107–110° C.; $^1$H-NMR(CDCl$_3$): δ 2.49(s, 3H), 3.16(s, 3H), 3.86(s, 3H) 7.16(d, J=8.3 Hz, 1H), 7.26(d, J=8.3 Hz, 1H), 7.85(s, 1H), 7.86(s, 1H). IR(KBr): 3450, 2925, 1710, 1620, 1440, 1370, 1120, 800, 740 cm$^{-1}$. MS m/z 333(M$^+$).

To a solution of 5-methylindole (77 mg, 0.66 mmol) dissolved in toluene (1 mL) was added 0.95M ethylmagnesium bromide (0.7 mL, 0.66 mmol) at 40° C., and the whole was stirred at 40° C. for 45 minutes. Successively, a solution of 2-bromo-3-(1,5-dimethyl-1H-indol-3-yl)-N-methylmaleimide (100 mg, 0.3 mmol) dissolved in toluene (5 mL) was added thereto, followed by stirring under heating and refluxing for 3 hours. After 20% aqueous citric acid solution (1 mL) was added thereto under ice cooling and the whole was stirred, toluene was removed by concentration under reduced pressure and the resulting concentrate was extracted with ethyl acetate. The extract was dried over sodium sulfate and then concentrated under reduced pressure. The residue was purified by column chromatography over silica gel (ethyl acetate:n-hexane=1:2) to obtain 2-(1,5-dimethyl-1H-indol-3-yl)-3-(5-methyl-1H-indol-3-yl)-N-methylmaleimide (100 mg, 86.9%) as red solids.

mp:110–112° C.; $^1$H-NMR(CDCl$_3$): δ 2.02(s, 3H), 2.09(s, 3H), 3.18(s, 3H), 3.77(s, 3H), 6.61(s, 1H), 6.79(s, 1H), 6.89(d, J=8.7 Hz, 1H), 6.92(d, J=8.7 Hz, 1H), 7.14(d, J=8.7 Hz, 1H), 7.18(d, J=8.7 Hz, 1H), 7.53(d, J=2.7 Hz, 1H), 7.59(s, 1H), 8.45(br s, 1H). IR(KBr): 3400, 2925, 1695, 1530, 1440, 1390, 1370, 800, 735 cm$^{-1}$. MS m/z 383(M$^+$).

To a solution of 2-(1,5-dimethyl-1H-indol-3-yl)-3-(5-methyl-1H-indol-3-yl)-N-methylmaleimide (100 mg, 0.26 mmol) in DMF (5 mL) was added a small amount of 10% palladium-carbon, and the whole was stirred at room temperature for 1 day under hydrogen atmosphere. The palladium-carbon was removed by filtration, and the filtrate was concentrated under reduced pressure. The residue was purified by column chromatography over silica gel (ethyl acetate:n-hexane =2:1) to obtain 3-(1,5-dimethyl-1H-indol-3-yl)-4-(5-methyl-1H-indol-3-yl)-1-methyl-2,5-dioxopyrrolidine (71 mg, 70.2%) as pale red solids.

mp:103–105° C.; $^1$H-NMR(CDCl$_3$): δ 2.31(s, 3H), 2.33(s, 3H), 3.27(s, 3H), 3.38(s, 3H), 4.76(s, 2H), 6.50(s, 1H), 6.55(d, J=2.5 Hz, 1H), 6.83(d, J=8.3 Hz, 1H), 6.87(d, J=8.3 Hz, 1H), 6.92(d, J=8.3 Hz, 2H), 6.99(s, 1H), 7.03(s, 1H), 7.61(br s, 1H). IR(KBr): 3375, 2920, 1695, 1530, 1440, 1390, 1370, 800 cm$^{-1}$. MS m/z 385(M$^+$).

To a solution of 3-(1,5-dimethyl-1H-indol-3-yl)-4-(5-methyl-1H-indol-3-yl)-1-methyl-2,5-dioxopyrrolidine (65 mg, 0.17 mmol) in THF (1.5 mL) was added 0.94M diisobutylaluminum hydride (0.72 mL, 0.68 mmol) dropwise slowly under ice cooling. After stirring at room temperature for 4 hours, the reaction mixture was added with saturated aqueous ammonium chloride solution and then stirred for further 30 minutes. Insoluble matter was removed by filtration through celite, and the filtrate was concentrated under reduced pressure. The residue was purified by column chromatography over silica gel (ethyl acetate:n-hexane=1:1) to obtain Compound 24 (34.8 mg, 58.4%) as colorless solids.

mp:75–81° C.; $^1$H-NMR(CDCl$_3$): δ 2.38(s, 3H), 2.42(s, 3H), 3.62(s, 3H), 3.79(s, 3H), 6.77(s, 1H), 6.86(s, 1H), 6.87(s, 1H), 6.96(d, J=2.3 Hz, 1H), 6.99(d, J=8.6 Hz, 1H), 7.02(d, J=8.6 Hz, 1H), 7.17(d, J=8.6 Hz, 1H), 7.22(d, J=8.6 Hz, 1H), 7.40(s, 1H), 7.51(s, 1H), 7.77(br s, 1H). IR(KBr): 3400, 2925, 2860, 1720, 1520, 1490, 1460, 1420, 1235, 1180, 790 cm$^{-1}$. MS m/z 353(M$^+$).

Sodium hydride (60 to 72%, oily, 20 mg) was washed with pentane and then suspended into DMF (2 mL). A DMF solution (2 mL) of Compound 24 (89 mg, 0.25 mmol) was added thereto, and the whole was stirred at room temperature for 45 minutes. On the other hand, DMF (0.5 mL) was added under ice cooling to a mixture of 3-chloropropylamine hydrochloride (33 mg, 0.25 mmol) and sodium hydride (60 to 72%, oily, 10 mg) washed with pentane, and the whole was stirred for 5 minutes and then warmed to room temperature with standing. The supernatant was added to the solution of sodium salt of 3-(1,5-dimethyl-1H-indol-3-yl)-4-(5-methyl-1H-indol-3-yl)-1-methylpyrrole. The resulting mixture was stirred at 40° C. for 1.5 hour, and then concentrated under reduced pressure to remove DMF. To the residue were added dichloromethane and saturated aqueous sodium chloride solution, and the organic layer was separated. The water layer was extracted with dichloromethane. The resulting organic layers were combined and dried over sodium sulfate. The residue obtained by removing the solvent under reduced pressure was purified by column chromatography over silica gel (chloroform saturated with ammonia:methanol=10:1) to obtain Compound 16 (78.9 mg, 76.3%) as pale orange solids.

mp:90–96° C.; $^1$H-NMR(CDCl): δ 1.31(br s, 2H), 1.73(tt, J=6.7, 6.7 Hz, 2H), 2.34(s,3H), 2.43(t, J=6.7 Hz, 2H), 2.45(s, 3H), 3.66(s, 3H), 3.79(s, 3H), 4.00(t, J=6.7 Hz, 2H), 6.74(s, 1H), 6.81(s, 1H), 6.84(d, J=2.3 Hz, 1H), 6.94(d, J=2.3 Hz, 1H), 7.00(d, J=8.0 Hz, 1H), 7.02(d, J=8.0 Hz, 1H), 7.17(d J=8.0 Hz, 1H), 7.20(d, J=8.0 Hz, 1H), 7.43(s, 1H), 7.56(s, 1H). IR(KBr): 3400, 2925, 2855, 1670, 1610, 1520, 1490, 1460, 1180, 790 cm$^{-1}$. MS m/z: 410(M$^+$).

Example 16

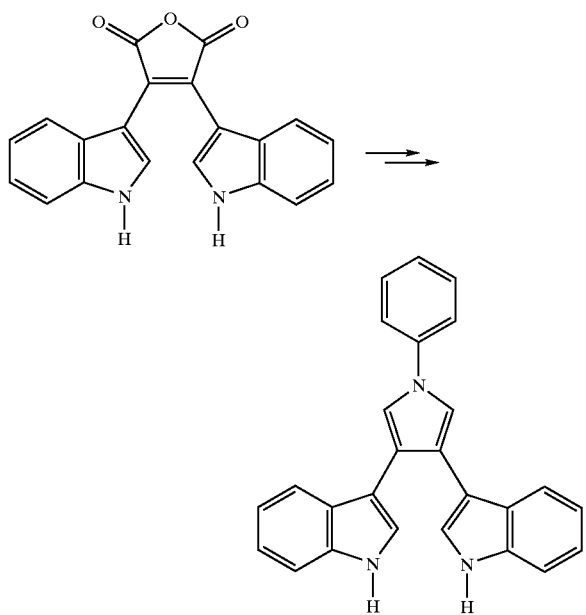

To a solution of 2,3-bis(1H-indol-3-yl)maleic anhydride (100 mg, 0.3 mmol) synthesized according to a known method (Tetrahedron, Vol. 44, p. 2887, 1988) and dissolved in DMF (10 mL) and water (10 mL) was added anilne (0.12 mL, 1.2 mmol), and the whole was stirred at 100 ° C. for 2 hours. The reaction mixture was concentrated under reduced pressure to remove DMF, and the concentrate was extracted with ethyl acetate. The extract was washed with water, dried over sodium sulfate, and then concentrated under reduced pressure. The residue was purified by column chromatography over silica gel (ethyl acetate:n-hexane=2:1) to obtain 2,3-bis(1H-indol-3-yl)N-phenylmaleimide (116 mg, 94.4%) as red solids.

mp: >290° C.; $^1$H-NMR (CDCl$_3$): δ 7.7(t, J=7.1 Hz, 2H), 7. 04 (d, J=7.1 Hz, 2H), 7.10(t, J=7.1 HZ, 2H), 7.36(d, J=7.1 Hz, 2H), 7.35–7.45(m, 1H), 7.48–7.55(m, 4H), 7.85(t, J=2.8 Hz, 2H), 8.54(br s, 2H). IR(KBr): 3365, 1700, 1525, 1430, 1390, 1245, 1120, 740 cm$^{-1}$. MS m/z 403(M$^+$).

A small amount of 10% palladium-carbon was added to a solution of 2,3-bis(1H-indol-3-yl)N-phenylmaleimide (55 mg, 0.14 mmol) dissolved in DMF (2 mL), and the whole was stirred at room temperature for 1 day under hydrogen atmosphere. The palladium-carbon was removed by filtration, and the filtrate was concentrated under reduced pressure. The residue was purified by column chromatography over silica gel (ethyl acetate:n-hexane=2:1) to obtain 3,4-bis(1H-indol-3-yl)-1-phenyl-2,5-dioxopyrrolidine (36 mg, 56.1%) as pale red solids.

mp: 260–263° C.; $^1$H-NMR(CDCl$_3$): δ 4.92(s, 2H), 6.61–6.70(m, 2H), 6.87–7.09(m, 6H), 7.30–7.60(m, 7H), 7.64(br s, 2H). IR(KBr): 3440, 3400, 1700, 1380, 1180, 750 cm$^{-1}$. MS m/z 405(M$^+$).

To a solution of 3,4-bis(1H-indol-3-yl)-1-phenyl-2,5-dioxopyrrolidine (30 mg, 0.07 mmol) in THF (1 mL) was added 0.94M diisobutylaluminum hydride (0.3 mL, 0.29 mmol) dropwise slowly under ice cooling. After stirring at room temperature for 4 hours, the reaction mixture was added with saturated aqueous ammonium chloride solution and then stirred for further 30 minutes. Insoluble matter was removed by filtration through celite, and the filtrate was concentrated under reduced pressure. The residue was purified by column chromatography over silica gel (ethyl acetate:n-hexane=1:1) to obtain Compound 17 (18.5 mg, 67.0%) as colorless solids.

mp: 109–111° C.; $^1$H-NMR(CDCl$_3$): δ 6.93(d, J=2.4 Hz, 2H), 7.05–7.56(m, 13H), 7.70(d. J=8.0 Hz, 2H), 7.86(br s, 2H). IR(KBr): 3400, 1600, 1510, 1450, 1420, 1240, 740 cm$^{-1}$. MS m/z: 373(M$^+$).

Example 17

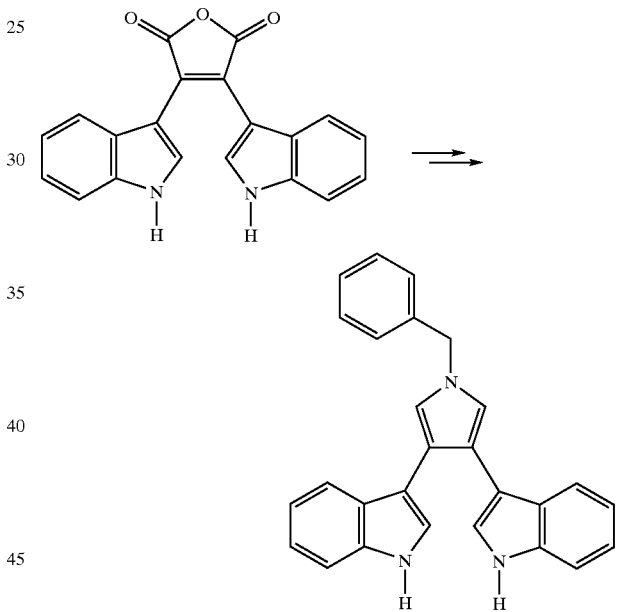

To a solution of 2,3-bis(1H-indol-3-yl)maleic anhydride (100 mg, 0.3 mmol) synthesized according to a known method (Tetrahedron, Vol. 44, p. 2887, 1988) and dissolved in DMF (10 mL) and water (10 mL) was added benzylamine (0.13 mL, 1.2 mmol), and the whole was stirred at 100 ° C. for 2 hours. The reaction mixture was concentrated under reduced pressure to remove DMF, and the concentrate was extracted with ethyl acetate. The extract was washed with water, dried over sodium sulfate, and then concentrated under reduced pressure. The residue was purified by column chromatography over silica gel (ethyl acetate:n-hexane=2:1) to obtain 2,3-bis(1H-indol-3-yl)-N-benzylmaleimide (110 mg, 86.6%) as red solids.

mp: >290° C. $^1$H-NMR(CDCl$_3$): δ 4.86(s, 2H), 6.75(t, J=8.0 Hz, 2H), 6.97(d, J=8.0 Hz, 2H), 7.06(t, J=8.0 Hz, 2H), 7.28–7.38(m, 5H), 7.50(d, J=8.0 Hz, 2H), 7.78(d, J=2.8 Hz, 2H), 8.49(br s, 2H). IR(KBr): 3400, 1695, 1530, 1430, 1405, 750 cm$^{-1}$. MS m/z: 417(M$^+$).

To a solution of 2,3-bis(1H-indol-3-yl)-N-benzylmaleimide (35 mg, 0.084 mmol) in DMF (1 mL) was added a small amount of 10% palladium-carbon, and the whole was stirred at room temperature for 6 hours under hydrogen atmosphere. The palladium-carbon was removed by filtration, and the filtrate was concentrated under reduced pressure. The residue was purified by column chromatography over silica gel (ethyl acetate:n-hexane=2:1) to obtain 3,4-bis(1H-indol-3-yl)-1-benzyl-2,5-dioxopyrrolidine (32.1 mg, 91.3%) as pale red solids.

mp: 112–115° C.; $^1$H-NMR(CDCl$_3$): δ 4.81(s, 2H), 4.95 (s, 2H), 6.60(d, J=2.5 Hz, 2H), 6.79–6.90(m, 2H), 6.91–7.11 (m, 6H), 7.30–7.45(m, 3H), 7.52–7.75(m, 4H) IR(KBr): 3410, 1700, 1400, 1345, 1165, 745 cm$^{-1}$. MS m/z: 419(M$^+$).

To a solution of 3,4-bis(1H-indol-3-yl)-1-benzyl-2,5-dioxopyrrolidine (30 mg, 0.07 mmol) in THF (1 mL) was added 0.94M diisobutylaluminum hydride (0.3 mL, 0.29 mmol) dropwise slowly under ice cooling. After stirring at room temperature for 4 hours, the reaction mixture was added with saturated aqueous ammonium chloride solution and then stirred for further 30 minutes. Insoluble matter was removed by filtration through celite, and the filtrate was concentrated under reduced pressure. The residue was purified by column chromatography over silica gel (ethyl acetate:n-hexane=1:1) to obtain Compound 18 (15 mg, 54.1%) as colorless solids.

mp: 119–121° C.; $^1$H-NMR(CDCl$_3$): δ 5.18(s, 2H), 6.94 (d, J=2.4 Hz, 2H), 7.00(s, 2H), 7.04(t, J=7.9 Hz, 2H), 7.14(t, J=7.9 Hz, 2H), 7.23–7.42(m, 7H), 7.63(d, J=7.9 Hz, 2H), 7.88(br s, 2H). IR(KBr): 3400, 1710, 1655, 1455, 1425, 1245, 745 cm$^{-1}$. MS m/z: 387(M$^+$).

Example 18

To a solution of Compound 16 (7 mg, 0.017 mmol) in dichloromethane (0.5 mL) was added a solution of 5(6)-carboxyfluorescein N-hydroxysuccinimidyl ester (9.5 mg, 0.017 mmol) in dichloromethane (0.5 mL). The resulting solution was kept away from light and stirred for 4.5 hours. Dichloromethane (3 mL) was added to the reaction mixture, and the mixture was washed with water. The organic layer was dried over magnesium sulfate and then concentrated under reduced pressure. The residue was purified by column chromatography over silica gel (ethyl acetate:n-hexane=2:1) to obtain Compound 19 (9.3 mg, 64.5%) as a mixture of two isomers as pale brown solids.

mp: 158–161° C.; $^1$H-NMR(CDCl$_3$): δ 1.90(tt, J=6.7, 6.7 Hz, 2H), 2.30(s, 6H), 2.32(s, 3H), 2.46(s, 3H), 3.05(dt, J=6.7, 6.7 Hz, 2H), 3.57(s, 3H), 3.80(s, 3H), 4.02(t, J=6.7 Hz, 2H), 5.44(t, J=6.7 Hz, 1H), 6.67–8.40(m, 19H). IR(KBr): 3400, 2945, 1770, 1610, 1500, 1425, 1370, 1200, 1110, 895, 795 cm$^{-1}$.

Example 19

-continued

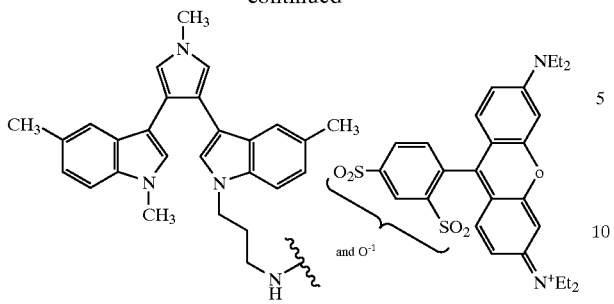

-continued

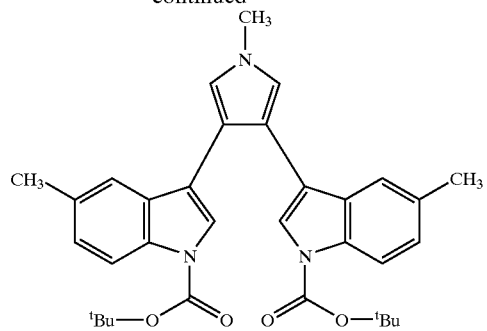

A solution of rhodamine B sulfonylchloride (14 mg, 0.024 mmol) in DMF (0.5 mL) was added to a mixture containing Compound 16 (10 mg, 0.024 mmol), N,N-diisopropylethylamine (3.4 μL, 0.024 mmol) in DMF (0.5 mL). The resulting mixture was kept away from light and stirred for 10 hours at room temperature. The reaction mixture was concentrated under reduced pressure to remove DMF. The residue was purified by column chromatography over silica gel (chloroform:methanol=10:1) to obtain Compound 20 (13 mg, 56.1%) and Compound 21 (7.3 mg, 31.5%) as purple solids.

Compound 20 mp: 176–180° C.; $^1$H-NMR(CDCl$_3$): δ 1.20–1.40(m, 12H), 1.80–1.92(m, 2H), 2.24(s, 3H), 2.41(s, 3H), 2.57–2.74 (m, 2H), 3.35–3.60(m, 8H), 3.73(s, 3H), 3.77(s, 3H), 3.90–4.10(m, 2H), 6.60–8.85(m, 20H). IR(KBr)3450, 2925, 1590, 1420, 1340, 1180 cm$^{-1}$.

Compound 21 mp: 164–169° C.; $^1$H-NMR(CDCl$_3$): δ 1.20–1.43(m, 12H), 1.60–1.85(m, 2H), 2.27(s, 3H), 2.36(s, 3H), 2.60–2.82 (m, 2H), 3.45–3.60(m, 8H), 3.57(s, 3H), 3.76(s, 3H), 3.80–3.91(m, 2H), 6.55–8.80(m, 20H). IR(KBr): 3450, 2925, 1590, 1420, 1340, 1180 cm$^{-1}$

Example 20

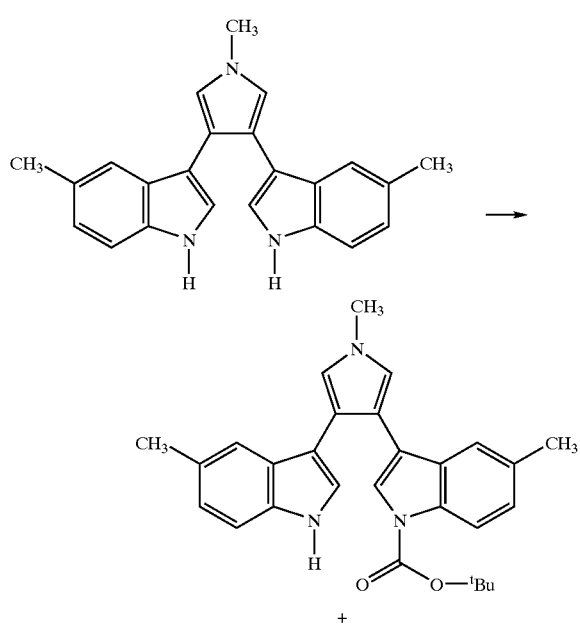

To a solution of Compound 15 (20 mg, 0.06 mmol) dissolved in THF (1 mL) were added di-tert-butyl dicarbonate (39 mg, 0.18 mmol) and a small amount of dimethylaminopyridine under ice cooling, and the whole was stirred for overnight at room temperature. The reaction mixture was concentrated under reduced pressure and the residue was purified by column chromatography over silica gel (ethyl acetate:n-hexane=1:3) to obtain Compound 22 (8 mg, 30.9%) and Compound 23 (20 mg, 62.9%) as pale yellow solids.

Compound 22 mp: 97–100° C.; $^1$H-NMR(CDCl$_3$): δ 1.56(br s, 9H), 2.28(s, 3H), 2.44(s, 3H), 3.81(s, 3H), 6.86(d, J=2.0 Hz, 1H), 6.89(d, J=2.0 Hz, 1H), 6.98(d, J=2.8 Hz, 1H), 7.00(d, J=8.7 Hz, 1H), 7.07(d, J=8.7 Hz, 1H), 7.20–7.24(m, 2H), 7.34(br s, 1H), 7.52(s, 1H), 7.82(s, 1H), 7.99(br s, 1H). IR(KBr): 3400, 2975, 2925, 1730, 1475, 1365, 1250, 1160, 800 cm$^{-1}$. MS m/z: 439(M$^+$).

Compound 23 mp: 93–97° C.; $^1$H-NMR(CDCl$_3$): δ 1.53(br s, 18H), 2.36(s, 6H), 3.81(s, 3H), 6.95(s, 2H), 7.09(d, J=8.0 Hz, 2H), 7.27(d, J=8.0 Hz, 2H), 7.32(s, 2H), 8.00(br s, 2H). IR(KBr): 3450, 2970, 2925, 1735, 1480, 1370, 1260, 1160, 1060, 800, 760 cm$^{-1}$. MS m/z: 539(M$^+$).

Test Example 1

Porcine ovaries were washed with PBS buffer, and Porcine ovarian granulosa cells (POGC) were collected by aspiration from follicles with a syringe. Cell fraction was recovered as a precipitate by centrifugation of the suspension. The operation of suspending the cell fraction into PBS buffer and subjecting the resulting suspension to centrifugation was repeated three times to wash the cells. The POGC obtained as a precipitate were suspended again into a culture medium (DMEM containing 10% fetal bovine serum) and cell clumps were disrupted by pipetting. The cell suspension was passed through a mesh to remove contaminating tissue fragments, and then pipetted in 24-well plates for cell culture. The cell suspension was cultured for 2 days in a CO$_2$ incubator according to a conventional procedure (37° C., 5% CO$_2$). Then, the medium was refreshed to remove floating cells and the cultivation was continued further 2 to 3 days until the cells reached subconfluency (0.7 to 2×105 cell/well). After the attaching cells were washed with serum-free medium, they were cultured in a serum-free DMEM (containing 5 μg/mL of transferrin, and 40 ng/mL of hydrocortisone, 4 mg/mL of bovine serum albumin (BSA), 100 nM androstendione) and it was possible to continue to culture cells with relatively immature differentiation. Addition of SNP (sodium nitroprusside, Na$_2$[Fe(CN)$_5$NO], 0.5 mM) known as an NO generating reagent to POGC cultured by the above method resulted in death of all the cells which was found on an observation after 6 hours under a light microscopy and an electron microscopy. The cell death was also confirmed by MTT assay. Then, various concentrations of the test compounds were added to the present culture system and the cells were observed after 18 hours. The results are shown in Table 1 where a minimum effective concentration of each compound for more than 95% of inhibition of cell death is described.

TABLE 1

Inhibiting Effects on Apoptosis of Porcine Ovarian Granulosa Cells by SNP stimulation

| Compound | MEC ($\mu$M) | Compound | MEC ($\mu$M) |
|---|---|---|---|
| 1 | 0.3 | 13 | 0.3 |
| 2 | 0.3 | 14 | 1 |
| 3 | 10 | 15 | 0.05 |
| 4 | 0.3 | 16 | 0.1 |
| 5 | 0.1 | 17 | 0.3 |
| 6 | 0.3 | 18 | 0.3 |
| 7 | 1 | 19 | 10 |
| 8 | 0.3 | 20 | 10 |
| 9 | 0.3 | 21 | 10 |
| 10 | 0.03 | 22 | 0.3 |
| 11 | 0.1 | 23 | 10 |
| 12 | 1 | 24 | 0.1 |

MEC : Minimum effective concentration

Test Example 2

When hydrogen peroxide (100 $\mu$M) was added to undifferentiated POGC, prepared by the method described in Test Example 1, all cells underwent to cell death characteristic of apoptotic morphological changes on an observation of 7 hours under a light microscopy. Test compound 16 (0.3 $\mu$M) was added to the above medium prior to the addition of hydrogen peroxide and cultivation was continued under the same condition cultured. An observation after 18 hour revealed complete inhibition of cell death and survival of more than 95% of the cells.

Test Example 3

According to a known method (A Dissection and Tissue Culture Manual of the Nervous System, p. 211, 1989, Alan R, Liss, Inc.), cerebellar granule cells were isolated from the cerebellum of 7 days old rats and cultured. Namely, after conducting isolation procedures described in the above literature, the resulting cells were resuspended in DMEM containing 10% fetal bovine serum, 25 mM KCl and 2 mM glutamine, and seeded in poly-lysine coated plates. After the cells were cultured in a $CO_2$ incubator for 48 hours according to a conventional method, cytosine-1-$\beta$-D(+)-arabinofuranoside (Ara-C) (10 $\mu$M) was added thereto, and the cell was continued to culture. The following experiments were conducted with the cells of 7 to 14 days old from the start day of the cultivation, the cells having completed neurite extension sufficiently. Addition of hydrogen peroxide (10 $\mu$M) to the cerebellar granule cells cultured as above resulted in death of all the cells, which was observed after 12 hours under a light microscopy. When the test compound 1 (10 $\mu$M) or the test compound 10 (10 $\mu$M) was added to the medium prior to the addition of hydrogen peroxide, observation similarly after 12 hours revealed that more than 80% or 95% of the cells, respectively, were alive.

Test Example 4

Neonatal jaundice is known to induce severe brain damages by way of abnormally high concentration of bilirubin in the body. This is likely caused by neuronal cell damages due to bilirubin. In fact, when bilirubin (10 $\mu$g/ml) was added to cerebellar granule cells cultured as described in Test Example 3, occurrence of cell death was observed under a light microscopy, and all cells were found to be dead on an observation after 23 hours. When the test compound 15 (10 $\mu$M) was added prior to the bilirubin addition, more than 95% of cells were alive on an observation made similarly after 23 hours.

Test Example 5

When SNP (100 $\mu$M) was added to cerebellar granule cells cultured as described in Test Example 3, occurrence of cell death was observed under a light microscopy, and all cells were found to be dead on an observation after 12 hours. When the test compound 1 (10 $\mu$M) or the test compound 10 (10 $\mu$M) was added prior to the SNP addition, more than 95% of cells in both cases were alive on an observation after 12 hours. In addition, when the test compound 15 (30 nM) was added, it inhibited cell death induced similarly by SNP (100 $\mu$M) and more than 95% of cells were alive on an observation after 24 hours.

Test Example 6

When sodium azide (10 mM), known as an inhibitor of respiration, was added to cerebellar granule cells cultured as described in Test Example 3, occurrence of cell death was observed under a light microscopy, and all cells were found to be dead on an observation after 2 hours. When the test compound 15 (10 $\mu$M) coexisted prior to the sodium azide addition, more than 95% of cells were alive on an observation made similarly after 2 hours.

Test Example 7

When antimycin A (5 $\mu$M), known as an inhibitor of respiration, was added to cerebellar granule cells cultured as described in Test Example 3, occurrence of cell death was observed under a light microscopy, and all cells were found to be dead on an observation after 2 hours. When the test compound 15 (10 $\mu$M) coexisted prior to the antimycin A addition, more than 95% of cells were alive on an observation made similarly after 2 hours.

Test Example 8

When FCCP (carbonyl cyanide p-(trifluoromethoxy) phenylhydrazone, 5 $\mu$M), known as an uncoupler of mitochondrial oxidative phosphorylation, was added to cerebellar granule cells cultured as described in Test Example 3, occurrence of cell death was observed under a light microscopy, and 90% of cells were found to be dead on an observation after 2 hours. When the test compound 15 (10 $\mu$M) coexisted prior to the FCCP addition, 80% of cells were alive on an observation similarly made after 2 hours.

Test Example 9

It is known that neuronal cells undergo cell death when they are cultured in a medium of low potassium (Proc. Natl. Acad. Sci. U.S.A., volume 90, p 10989, 1993). In fact, when cerebellar granule cells cultured as described in Test Example 3 were transferred to a low potassium medium (5 mM KCl) and cultivation was continued, occurrence of cell death was observed under a light microscopy, and all cells were found to be dead on an observation after 18 hours. When the test compound 1 (10 $\mu$M), the test compound 10 (10 $\mu$M), or the test compound 15 (10 $\mu$M)coexisted, 50%, 80%, and 85% of cells were respectively alive on an observation made similarly after 18 hours.

Test Example 10

Medium of cerebellar granule cells cultured for 14 days as described in Test Example 3 was replaced with DMEM containing 10% of dialyzed fetal bovine serum and subjected to a further overnight culture. When glutamate (1 mM), known as a neurotransmitter, was added to this culture, occurrence of cell death was observed under a light microscopy as well as MTT assay, and more than 95% of cells were found to be dead on an observation after 2 hours. When the test compound 15 (10 μM) coexisted, more than 95% of cells were alive on an observation even after 6 hours.

Test Example 11

Hela 3S cells (culture medium: DMEM containing 10% fetal bovine serum), a cell line derived from human cervical cancer, were seeded into multi 48 well plates and cultured in a $CO_2$ incubator according to conventional procedures. Confirming the subconfluency of a cell culture, the medium was replaced with Krebs Ringer Buffer (120 mM NaCl, 50 mM KCl, 1 mM $KH_2PO_4$, 200 mM $NaHCO_3$, 20 mM HEPES, pH 7.4, 2.57 g/L glucose, 0.05 g/L Phenol Red) and washed three times with the same buffer and cultivation continued in the same buffer. An observation under a light microscopy after 5 hours showed 42% of the cells carrying nuclear condensation and blebbing of plasma membrane characteristic of the apoptotic process, 11% of necrosis-like swollen cells (whose loss of a function of the plasma membranes were confirmed by the trypan blue exclusion test), and 42% of the cells showing normal cell shapes. When the test compound 1 (10 μM) or the test compound 15 (10 μM) was added in the present culture system and cultivation continued similarly, the proportion of normal cells increased 59% or 77% respectively, and the proportion of necrosis-like cells decreased (1% or 0%, respectively), indicating the anti-cell death effects.

Test Example 12

Human blood was collected and precipitated by a centrifugation (1000 rpm, 5 min) and the precipitate containing erythrocytes was washed three times with PBS and resuspended (about $5 \times 10^8$ cells/ml) with DMEM containing 10% fetal bovine serum. Cell suspensions were dispensed into a 48-well plate to become subconfluent (about $5 \times 10^5$ cells/0.5 ml/well). When hydrogen peroxide (300 μM) was added and cultivation continued for 24 hours, more than 95% of erythrocytes underwent hemolysis and become dark and ghost-like on an observation under a light microscopy. When the test compound 1(10 μM), the test compound 10(10 μM), or the test compound 15 (10 μM) was added prior to the addition of hydrogen peroxide, observation made after 24 hours revealed almost complete inhibition of hemolysis.

Test Example 13

In Parkinson's disease the dopaminergic neurons in the substantia nigra and corpus striatum in the mid-brain are selectively destroyed. Because following administration of MPTP(1-methyl-4-phenyl-1,2,3,6-tetrahydropyridine) the similar selective destruction of the dopaminergic neurons and Parkinson's disease-like symptoms are observed, the administration system of MPTP is generally employed as an in vivo model of the onset of Parkinson's disease. Since MPTP is known to exert its effect via its conversion to MPP+(1-methyl-4-phenylpyridinium) by MAO-B (monoamine oxidase type B)in the substantia nigra of the mid-brain, 1-methyl-4-phenylpyridinium iodide (MPPI),an oxidative type of MPTP, is used for tests at cellular levels (a reference of a Parkinson model with use of cerebellar granule cells: J. Neuroscience, volume 9, p 3665, 1989). When MPPI (200 μM) was added to 15 DIV cerebellar granule cells cultured as described in Test Example 3, all cells were found to be dead on an observation after 18 hours. When the test compound 15 (1 μM) was added prior to the MPPI addition, more than 95% of cells were alive on the same observation after 18 hours. The judgement of cell death was conducted under a light microscopy, which was, moreover, confirmed by the trypan blue-exclusion test as well as LDH (lactate dehydrogenase)-leakage assay.

The above results demonstrated that the compounds according to the present invention are able to inhibit cell death in response to a variety of stimuli in various cell types.

Industrial Applicability

Since the bisindolylpyrrole derivatives according to the present invention inhibit cell death caused by a wide variety of cell death-inducing stimuli, they are considered to be useful for prevention or treatment of all the diseases whose onset and exacerbation are associated with cell death. Accordingly, the derivatives have uses as remedies for neurodegenerative diseases such as Alzheimer's disease, spinal muscular atrophy, amyotrophic lateral screrosis, Parkinson's disease, Huntington's disease, pigmentary degeneration of the retina, glaucoma, cerebellar degeneration and neonatal jaundice; myasthenia gravis; brain ischemia from apoplexy and the like, and successive delayed neuronal death, ischemic heart disease due to myocardial infarction (myocardial ischemia and disorder after reperfusion); viral myocarditis; autoimmune myocarditis (congestive cardiomyopathy and chronic myocarditis); myocardial disorders or death due to hypertrophic heart and heart failure; arrythmogenic right ventricular cardiomyopathy; alcoholic hepatitis and viral hepatitis; renal diseases such as glomerulonephritis, hemolytic uremic syndrome and the like; acquired immunodeficiency syndrome (AIDS); inflammatory skin disorders such as toxic epidermal necrolysis (TEN) and multiform exudative erythema; alopecia; graft versus host disease (GVH); radiation disorders; disorders due to toxic agents including side effects due to anti-cancer drugs, anti-viral drugs and the like; sepsis; osteomyelodysplasia such as aplastic anemia and the like; insulin dependent diabetes; prion diseases such as Creutzfeldt-Jakob's disease and the like; and functional deficiency of transplanted organs and the like, or uses as drugs for stopping or inhibiting progress and exacerbation of the diseases; and also uses as preservatives for organs, tissues and cells.

What is claimed is:

1. A bisindolylpyrrole derivative represented by the following formula [I]

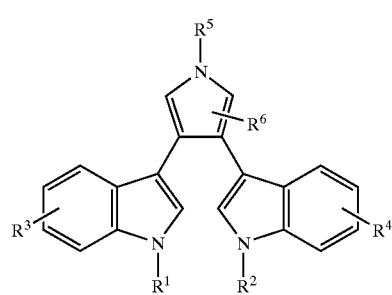

wherein, $R^1$ and $R^2$ each independently represents hydrogen atom, an alkyl group which may possess substituent(s), an alkenyl group which may possess substituent(s), an alkynyl group which may possess substituent(s), an aryl group which may possess substituent(s), an acyl group which may possess substituent(s), an acyloxy group which may possess substituent(s), an alkoxy- or aryloxycarbonyl group which may possess substituent(s), an alkyl- or arylthiocarbonyl group which may possess substituent(s), an aminocarbonyl group which may possess substituent(s), an aminocarbonyloxy group which may possess substituent(s), an alkyl- or arylsulfonyl group which may possess substituent(s), an alkoxyl group which may possess substituent(s), an aryloxy group which may possess substituent(s), or hydroxyl group; $R^3$ and $R^4$ each represents substituent(s) on an indole ring, and represents, number and position (2-, 4-, 5-, 6-, or 7-position as position number of the indole ring) of the substituent(s) and kinds of the substituent(s) may be the same or different, hydrogen atom, an alkyl group which may possess substituent(s), an alkenyl group which may possess substituent(s), an alkynyl group which may possess substituent(s), an aryl group which may possess substituent(s), an acyl group which may possess substituent(s), an acyloxy group which may possess substituent(s), an alkoxy- or aryloxycarbonyl group which may possess substituent(s), an alkoxy- or aryloxycarbonyloxy group which may possess substituent(s), an alkyl- or arylthiocarbonyl group which may possess substituent(s), an aminocarbonyl group which may possess substituent(s), an aminocarbonyloxy group which may possess substituent(s), an alkyl- or arylsulfonyl group which may possess substituent(s), an alkyl- or arylsulfinyl group which may possess substituent(s), an alkoxyl group which may possess substituent(s), an aryloxy group which may possess substituent(s), an alkyl- or arylthio group which may possess substituent(s), hydroxyl group, carboxyl group, oxysulfonyl group, cyano group, nitro group, an amino group which may possess substituent(s), or a halogen atom; $R^1$ and $R^2$, $R^1$ and $R^3$, $R^2$ and $R^4$, $R^3$ and $R^6$, $R^5$ and $R^6$, two $R^3$, or two $R^4$ may be combined to form a hydrocarbon chain or a hydrocarbon chain containing heteroatom(s) which may possess substituent(s); $R^5$ represents hydrogen atom, an alkyl group which may possess substituent(s), an alkenyl group which may possess substituent(s), an alkynyl group which may possess substituent(s), an aryl group which may possess substituent(s), hydroxyl group, an alkoxyl group which may possess substituent(s), an aryloxy group which may possess substituent(s), an amino group which may possess substituent(s), an acyl group which may possess substituent(s), an acyloxy group which may possess substituent(s), an alkoxy- or aryloxycarbonyl group which may possess substituent(s), an alkyl- or arylthio group which may possess substituent(s), an aminocarbonyl group which may possess substituent(s), an alkyl- or arylsulfonyl group which may possess substituent(s); $R^6$ represents substituent(s) on a pyrrole ring (at 2-, 5-, or both position(s) as position numbering of pyrrole ring, in the last case substituents may be the same or different), hydrogen atom, an alkyl group which may possess substituent(s), an alkenyl group which may possess substituent(s), an alkynyl group which may possess substituent(s), an aryl group which may possess substituent(s), an acyl group which may possess substituent(s), an acyloxy group which may possess substituent(s), an aryloxycarbonyl group which may possess substituent(s), an aryloxycarbonyloxy group which may possess substituent(s), an alkyl- or arylthiocarbonyl group which may possess substituent(s), an aminocarbonyl group which may possess substituent(s), an aminocarbonyloxy group which may possess substituent(s), an alkyl- or arylsulfonyl group, an alkyl- or arylsulfinyl group which may possess substituent(s), an alkoxyl group which may possess substituent(s), an aryloxy group which may possess substituent(s), an alkyl- or arylthio group which may possess substituent(s), hydroxyl group, carboxyl group, oxysulfonyl group, cyano group, nitro group, an amino group which may possess substituent(s), or a halogen atom.

2. A pharmaceutical composition comprising, as an active ingredient, a bisindolylpyrrole derivative represented by the following formula or a pharmaceutically acceptable salt thereof

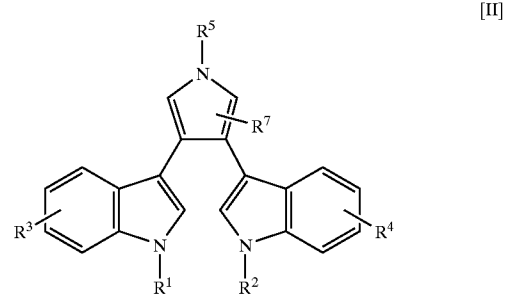

[II]

wherein, $R^1$ and $R^2$ each independently represents hydrogen atom, an alkyl group which may possess substituent(s), an alkenyl group which may possess substituent(s), an alkynyl group, which may possess substituent(s), an aryl group which may possess substituent(s), an acyl group which may possess substituent(s), an acyloxy group which may possess substituent(s), an alkoxy- or aryloxycarbonyl group which may possess substituent(s), an alkyl- or arylthiocarbonyl group which may possess substituent(s), an aminocarbonyl group which may possess substituent(s), an aminocarbonyloxy group which may possess substituent(s), an alkyl- or arylsulfonyl group which may possess substituent(s), an alkoxyl group which may possess substituent(s), an aryloxy group which may possess substituent(s), or hydroxyl group; $R^3$ and $R^4$ each represents substituent(s) on an indole ring, and represents, number and position (2-, 4-, 5-, 6-, or 7-position as position number of the indole ring) of the substituent(s) and kinds of the substituent(s) may be the same or different, hydrogen atom, an alkyl group which may possess substituent(s), an alkenyl group which may possess substituent(s), an alkynyl group which may possess substituent(s), an aryl group which may possess substituent(s), an acyl group which may possess substituent(s), an acyloxy group which may possess substituent(s), an alkoxy- or aryloxycarbonyl group which may possess substituent(s), an alkoxy- or aryloxycarbonyloxy group which may possess substituent(s), an alkyl- or arylthiocarbonyl group which may possess substituent(s), an aminocarbonyl group which may possess substituent(s), an aminocarbonyloxy group which may possess substituent(s), an alkyl- or arylsulfonyl group which may possess substituent(s), an alkyl- or arylsulfinyl group which may possess substituent(s), an alkoxyl group which may possess substituent(s), an aryloxy group which may possess substituent(s), an alkyl- or arylthio group which may possess substituent(s), hydroxyl group, carboxyl group, oxysulfonyl group, cyano group, nitro group, an amino group which may possess substituent(s), or a halogen atom; $R^1$ and $R^2$, $R^1$ and $R^3$, $R^2$ and $R^4$, $R^3$ and $R^7$, $R^4$ and $R^7$, $R^5$ and $R^7$, two $R^3$, or two $R^4$ be combined to form a hydrocarbon chain or a hydrocarbon chain containing heteroatom(s) which may possess substituent(s); $R^5$ represents hydrogen atom, an alkyl group which may possess substituent(s), an alkenyl group which may possess substituent(s), an alkynyl group which may possess substituent(s), an aryl group which may possess substituent(s), hydroxyl group, an alkoxyl group which may possess substituent(s), an aryloxy group which may possess substituent(s), an amino group which may possess substituent(s), an acyl group which may possess substituent(s), an acyloxy group which may possess substituent(s), an alkoxy- or aryloxycarbonyl group which may possess substituent(s), an alkyl- or arylthiocarbonyl group which may possess substituent(s), an aminocarbonyl group which may possess substituent(s), an alkyl- or arylsulfonyl group which may possess substituent(s); $R^7$ represents substituent(s) on a pyrrole ring (at 2-, 5-, or both position(s) as position numbering of pyrrole ring, in the last case substituents may be the same or different), hydrogen atom, an alkyl group which may possess substituent(s), an alkenyl group which may possess substituent(s), an alkynyl group which may possess substituent(s), an aryl group which may possess substituent(s), an acyl group which may possess substituent(s), an acyloxy group which may possess substituent(s), an alkoxy- or an aryloxycarbonyl group which may possess substituent(s), an alkoxy- or an aryloxycarbonyloxy group which may possess substituent(s), an alkyl- or arylthiocarbonyl group which may possess substituent(s), an aminocarbonyl group which may possess substituent(s), an aminocarbonyloxy group which may possess substituent(s), an alkyl- or arylsulfonyl group, an alkyl- or arylsulfinyl group which may possess substituent(s), an alkoxyl group which may possess substituent(s), an aryloxy group which may possess substituent(s), an alkyl- or arylthio group which may possess substituent(s), hydroxyl group, carboxyl group, oxysulfonyl group, cyano group, nitro group, an amino group which may possess substituent(s), or a halogen atom, and a pharmaceutically acceptable carrier.

3. The composition of claim 2, wherein said composition is useful for inhibiting death of a cell.

4. The composition of claim 2, wherein said composition is useful for inhibiting death of a cell in a patient in need thereof.

5. The composition of claim 4 wherein said cell is selected from the group consisting of neurons, hepatic cells, bone marrow cells, T cells, renal cells and myocardial cells.

6. The composition of claim 2, wherein said composition is useful for treating a neurodegenerative disease.

7. The composition of claim 6, wherein said neurodegenerative disease is selected from the group consisting of Alzheimer's disease, spinal muscular atrophy, amyotrophic lateral sclerosis, Parkinson's disease, Huntington's disease, pigmentary degeneration of the retina, glaucoma and cerebellar degeneration.

8. The composition of claim 2, wherein said composition is useful for treating neonatal jaundice.

9. The composition of claim 2, wherein said composition is useful for treating myasthenia gravis.

10. The composition of claim 2, wherein said composition is useful for treating brain ischemia and delayed neuronal death (DND).

11. The composition of claim 2, wherein said composition is useful for treating ischemic heart disease, viral myocarditis, autoimmune myocarditis, myocardial disorders/cell death due to hypertrophic heart and heart failure, or arrythmogenic right ventricular cardiomyopathy.

12. The composition of claim 2, wherein said composition is useful for treating alcoholic hepatitis or viral hepatitis.

13. The composition of claim 2, wherein said composition is useful for treating renal disease.

14. The composition of claim 2, wherein said composition is useful for treating acquired immunodeficiency syndrome (AIDS).

15. The composition of claim 2, wherein said composition is useful for treating an inflammatory skin disorder, alopecia, or graft versus host disease (GVH).

16. The composition of claim 2, wherein said composition is useful for treating a disorder due to radiation or drugs.

17. The composition of claim 2, wherein said composition is useful for treating sepsis.

18. The composition of claim 2, wherein said composition is useful for treating osteomyelo-dysplasia.

19. The composition of claim 2, wherein said composition is useful for treating insulin dependent diabetes.

20. The composition of claim 2, wherein said composition is useful for treating a prion disease.

21. The composition of claim 2, wherein said composition is useful for treating or preventing functional deficiency of transplanted organs, tissues or cells in a patient in need thereof.

22. The composition of claim 2, wherein said composition is useful for preserving organs, tissues or cells.

* * * * *